(12) United States Patent
Yaver et al.

(10) Patent No.: US 6,667,169 B2
(45) Date of Patent: Dec. 23, 2003

(54) POLYPEPTIDES HAVING ACID PHOSPHATASE ACTIVITY AND NUCLEIC ACIDS ENCODING SAME

(75) Inventors: Debbie S. Yaver, Davis, CA (US); Randy M. Berka, Davis, CA (US); Michael W. Rey, Davis, CA (US)

(73) Assignee: Novozymes Biotech, Inc., Davis, CA (US)

( * ) Notice: Subject to any disclaimer, the term of this patent is extended or adjusted under 35 U.S.C. 154(b) by 0 days.

(21) Appl. No.: 09/957,156

(22) Filed: Sep. 19, 2001

(65) Prior Publication Data

US 2002/0164753 A1 Nov. 7, 2002

Related U.S. Application Data

(60) Division of application No. 09/483,371, filed on Jan. 14, 2000, now Pat. No. 6,309,869, which is a continuation-in-part of application No. 09/231,612, filed on Jan. 14, 1999, now abandoned.

(51) Int. Cl.[7] ............................. C12N 9/16; C12N 1/19; C12N 15/52; C12N 15/62; C07H 21/04
(52) U.S. Cl. ............... 435/196; 435/252.3; 435/252.33; 435/254.11; 435/254.2; 435/320.1; 435/325; 435/69.1; 435/69.7; 435/410; 536/23.2; 536/23.4; 536/23.7
(58) Field of Search ............................. 435/196, 252.3, 435/254.11, 254.2, 410, 325, 320.1, 69.1, 69.7, 252.33; 536/23.2, 23.7, 23.4

(56) References Cited

U.S. PATENT DOCUMENTS 5,268,273 A    12/1993   Buckholz

FOREIGN PATENT DOCUMENTS

EP        857788      12/1998

OTHER PUBLICATIONS

Saha et al.. 1985. Archives of Biochemistry & Biophysics 243: 150–160.
Gonzales & Meizel. 1973. Biochemica Biophysica Acta 320: 180–194.
Horgen et al.. 1974. Canadian Journal of Biochemistry 52: 126–136.
Lin & Clinton, 1987, In Merlevede & DiSalvo, editors, Adv. Prot. Phosphatases 4: 199–228.
Filburn. 1973. Archives In Biochemistry & Biophysics 159: 683–693.
Ferens & Morawiecka. 1985. Phytochemistry 24: 2839–2842.
Heredia et al., 1963, BioChem. Biophys. Res. Commun. 10: 14–18.
Gunther & Kattner, 1968, Z. Naturforsch 236: 77–80.
Roomans & Borst–Pauwels, 1979, Biochemical Journal 178: 521–527.
Etebarian et al., 1996, Iranian Journal of Plant Pathology 32: 9–21.
Sano & Ui, 1981, Annals of Phytopathological Society of Japan 47: 547–554.
Madhosingh, 1980, Phytopathological Zeitschrift 97: 56–67.
Yoshida, 1973, Journal of Biochem 73: 23–29.
Huss et al., 1993, Applied & Enviro. Microbio. 62: 3750–3756.
Pomazi et al.. 1993. Acta Microbiological Hungarica 40: 71–79.
Rodgers et al., 1982, Proceedings of the National Academy of Science USA 79: 2757–2161.

*Primary Examiner*—Elizabeth Slobodyansky
(74) *Attorney, Agent, or Firm*—Robert L. Starnes

(57) ABSTRACT

The present invention relates to isolated polypeptides having acid phosphatase activity and isolated nucleic acid sequences encoding the polypeptides. The invention also relates to nucleic acid constructs, vectors, and host cells comprising the nucleic acid sequences as well as methods for producing and using the polypeptides.

20 Claims, 6 Drawing Sheets

```
AATTAACTTGTTCTCTGGATGTCCTCCTTTGATCTTGTCCAAATAAGCTCAATTCCATCACACCATAAAG   70
GTGTAGAGTCAAGATGCGTCTGTCAACATATCCTCACTGGAGCAGCCCTGTTCTCGTCCTCACAGCTCTG  140
                M  R  L  S  T  I  L  T  G  A  A  L  F  S  S  Q  A  L
AACATCCCTTCTTAACAATGATGGATGGATTCGGATCTGCGAACTGCGCGTGAGATGTACCGTCTCTTCAAGG  210
 N  I  L  L  N  N  D  D  G  F  G  S  A  N  L  R  E  M  Y  R  L  F  K
AAAAGGGCCACAATGGTACCAAGCCTCCTTCATTTTCCAGGAACAATAACTGACATACCTTGACCAGT  280
 E  K  G  H  N                                                      V
CTGGCTCGTTGCACCAGCCACCAAGTGGCAAGTGGCGGTACCTCTGATTTCACCACCGAGGGCAAT  350
 W  L  V  A  P  A  T  K  Q  S  G  K  G  G  T  S  D  F  T  T  E  G  N
TTGACTGGACCCTTCTCAATACGATCTAATTCCCAAGGCGCCACCATCAGTATGATCACCAAGTACACGGG  420
 L  T  G  P  S  Q  Y  D  L  I  P  K  G  A  P  S
TCGCAATGAGATGAGACTAACAGATCTTTTTTAGGTCGGAAGTGATCCAAAGGATAGCCAAATCTGGTAC  490
                                      V  G  S  D  P  K  D  S  Q  I  W  Y
TACAATGGCACTCCTGCTGCGTGCACATTGTTGCTCTCCGACTATGTTCTCCCCGATACGCCAACTTTA  560
 Y  N  G  T  P  A  A  C  T  F  V  A  L  D  Y  V  L  P  R  Y  A  N  F
GCGTTCCTGACCTTGTCGTTTGACCCTTTTGACAGACCAACATTGATACTTACTTCCTTAGGTGA  630
                                                                      V
CTGGTCCTAACTATGGCACCAACTTGGGCGGTTTCGTGGGCTTCGTGGACTCTATCCGGTACTGCTGGTGTA  700
 T  G  P  N  Y  G  T  N  L  G  G  F  V  W  T  L  S  G  T  A  G  A
AGTCTTCAACACAACATGACTCAGTGAAACGTATAAAATACTGACAGGACTGTAGATACGCCGCTACAAACC  770
                                          Y  A  A  T  N
GTGGAATTCCCGCAATTGCCATATCAGCGAGCAACCAGGAAGTTCCCTACTTCGAACTGACAAACCGCAC  840
 R  G  I  P  A  I  A  S  A  S  N  Q  E  V  P  Y  F  E  L  T  N  R  T
CAACCCAGCTACGTGGGCTGCCCAAGCCTCGTAAATTCGTCGAGAACTTTATTCGACAGCTGGCAAG  910
 N  P  A  T  W  A  A  Q  A  S  V  K  F  V  E  N  F  I  S  T  A  G  K
AACGGTCCCCTTTGCCCTAGGGCGTCAATGTCAATCTTCCCGTGTTGACGAAGAAAGATCACG  980
 N  G  P  L  L  P  I  G  Y  G  V  N  V  N  L  P  V  L  T  K  K  D  H
```

Fig. 1A

```
ACCCCGAATTCGTGCAGACGAGGTTCACGGGCAATGCGCACGTTAACGAAGCGGTGCTTGATCCGAAGAA    1050
 D   P   E   F   V   Q   T   R   F   T   G   N   A   H   V   N   E   A   V   L   D   P   K   K
GGGAACGTTTACGTGGGCCAACATCAAGCCCTTATGCTCTGCGAATGCTTGTATCAATGGCAACTGC       1120
 G   T   F   T   W   A   N   I   K   P   Y   A   A   G   V   N   A   C   I   N   G   N   C
TCGCTGCCCGGTGAGACGTATGTTGTTGAGAACGGAAAGGCGTCTGTATCGTTTTATACAGTGGATTACA    1190
 S   L   P   G   E   T   Y   V   V   E   N   G   K   A   S   V   S   F   Y   T   V   D   Y
GTGCTCCCGAAACTGAGTACACCGAATCACTCGATCGAGTGGCGTCGTTCATTGGGAAATAAACAAG       1260
 S   A   P   E   T   E   Y   T   E   S   L   I   D   R   V   A   S   F   I   G   K    .
AAAGGACCAGCCCCGAAGTTGGTTAACAATGATCATAACAGATAATGATAGTATACATGT               1330
TGTTACATGACATGATGCGCCTGCTTTCCATATGCAATGCAATGCAAGTTCAATATTTCTTTCCC         1400
GCGCCACCTTCTCGATATCGAACGTCGATGTCCCGTCTCTTCCCACGCGTCTTCCATAGTCCTCAC        1470
CTTGATCAGCTCAACAGTGTCAGTCGCGGAAGGATTTTTGACATCTTTCCATAGTCCTTTCCACGTGGA     1540
TGTAGCTTTAGTAGCGGAACCTCTTCATAGGCCTTCAACGTCAACCGTTATGTACTAACAA             1610
GTGCTGGTTACGAGGCTCTTCATAGGCCTTCAACGTCAACCGTTATGTACTAACAA                  1680
ACTTCTGTGACGGCGACGAACTTCAAGAATGCCCCAGAGGTGCACGTGTAATGA                    1750
TTCTCTGACGGCGACGAACTTCAAGAATGCCCCAGAGGTGCACGTGTAATGA                      1820
CTCACCTATGTCACCCGGCTACTAATGTCGCGGACGACTTCTCAGTATACTTCGTTATCGACGAGTCCT     1890
GCAAATATGTCTAGTAATGTCGCGGACGACTTGGTGCTCTACCGATGACCATGGA                   1960
TGTCAGCTTGGAGACGAAGGAGCTTCAAGGATGTGCTGATAGAGCTCGAGTGTCAATGGGGATTTGACCT    2030
GGGAAGGTCCATGACACACCCAGAAGGATGTGCTGATAGAGCTCGAGTGTCAATGGGGATTTGACCT       2100
GGGTTTTAACTTGTGTTTCGCAACTAGAGTTAGCAAGTCGTGGGAAAACCCTGGCATAAA              2170
CTTGAAGCAACTGCACTAGAGTTAGCAAGTCATGTCAGTGAGCTCATGTCTCGGCATAAA              2240
GGGACAAACAGTGAAAAGTGAGAGTGAAATGAAAAATTCCCGGTCGACGTCATGCGACGTCATGCGGC      2310
CGCTCTAGAGGATCCAAGCTTGCCGTCGACGTCATGCGACGTCATGCGACTAAAT                   2380
TCAATTCACTGCCGTCGTTTTACAACGTCGTGCGTTACCAACTTAATGCCT                       2450
TGCAGCACATCCCCTTTCGCCAGCTGGGAAAACCCTGGCCGTTACCAACTTAATGCCT                2520
TTGCGCCAGCCTGAATGGCGAATGG    2544
```

Fig. 1B

POLYPEPTIDES HAVING ACID PHOSPHATASE ACTIVITY AND NUCLEIC ACIDS ENCODING SAME

CROSS-REFERENCE TO RELATED APPLICATION

This application is a divisional of U.S. application Ser. No. 09/483,371, filed on Jan. 14, 2000, now U.S. Pat. No. 6,309,869 which is a CIP of U.S. application Ser. No. 09/231,612, filed on Jan. 14, 1999, now abandoned, which applications are fully incorporated herein by reference.

BACKGROUND OF THE INVENTION

1. Field of the Invention

The present invention relates to isolated polypeptides having acid phosphatase activity and isolated nucleic acid sequences encoding the polypeptides. The invention also relates to nucleic acid constructs, vectors, and host cells comprising the nucleic acid sequences as well as methods for producing and using the polypeptides.

2. Description of the Related Art

Acid phosphatases (EC 3.1.3.2) catalyze the hydrolysis of an orthophosphate monoester to an alcohol and orthophosphate. The substrate specificity includes phosphomonoesters, nucleoside monophosphates, nucleoside diphosphates, nucleoside triphosphates, hexose monophosphates, and many other compounds (see, for example, Saha et al., 1985, *Archives of Biochemistry and Biophysics* 243: 150–160; Gonzales and Meizel, 1973, *Biochimica Biophysica Acta* 320: 180–194; Horgen et al., 1974, *Canadian Journal of Biochemistry* 52: 126–136).

Acid phosphatases play a physiological role in fertilization (Lin and Clinton, 1987, In Merlevede and DiSalvo, editors, *Adv. Prof. Phosphatases* 4: 199–228), epidermal growth (Lin and Clinton, 1987, supra), energy metabolism (Filburn, 1973, *Archives in Biochemistry and Biophysics* 159: 683–693), mobilization of phosphorus reserves during seed germination (Ferens and Morawiecka, 1985, *Phytochemistry* 24: 2839–2842); and scavenging phosphorus for growing cells (Heredia et al., 1963, *Biochem. Biophys. Res. Commun.* 10: 14–18; Günther and Kattner, 1968, *Z. Naturforsch* 236: 77–80; Roomans and Borst-Pauwels, 1979, *Biochemical Journal* 178: 521–527).

Acid phosphatases have been reported to be useful for the preparation of nucleoside 5'-phosphates from a nucleoside and a phosphate donor (EP 857788).

Acid phosphatases have been isolated from mammals, plants, bacteria, yeast and fungi. In particular, acid phosphatases have been reportedly produced by Fusarium strains including *Fusarium culmorum* (Etebarian et al., 1996, *Iranian Journal of Plant Pathology* 32: 9–21); *Fusarium solani* (Sano and Ui, 1981, *Annals of the Phytopathological Society of Japan* 47: 547–554; *Fusarium oxysporum* (Madhosingh, 1980, *Phytopathologische Zeitschrift* 97: 56–67); *Fusarium moniliforme* (Yoshida, 1973, *Journal of Biochemistry* 73: 23–29); and Fusarium sp. (Huss et al., 1996, *Applied and Environmental Microbiology* 62: 3750–3756; Min and Kweon, 1994, *Korean Journal of Mycology* 22: 386–393; Pomazi et al., 1993, *Acta Microbiologica Hungarica* 40: 71–79).

Acid phosphatase genes have been isolated from *Pichia pastoris* (U.S. Pat. No. 5,268,273) and *Saccharomyces cerevisiae* (Rodgers et al., 1982, *Proceedings of the National Academy of Sciences USA* 79: 2157–2161).

There is a need in the art for new acid phosphatases that can be produced in commercial quantities.

It is an object of the present invention to provide improved polypeptides having acid phosphatase activity and nucleic acid encoding the polypeptides.

SUMMARY OF THE INVENTION

The present invention relates to isolated polypeptides having acid phosphatase activity selected from the group consisting of:

(a) a polypeptide having an amino acid sequence which has at least 65% identity with amino acids 19 to 318 of SEQ ID NO. 2;

(b) a polypeptide encoded by a nucleic acid sequence which hybridizes under medium stringency conditions with (i) nucleotides 138 to 1252 of SEQ ID NO. 1, (ii) the cDNA sequence contained in nucleotides 138 to 1252 of SEQ ID NO. 1, (iii) a subsequence of (i) or (ii) of at least 100 nucleotides, or (iv) a complementary strand of (i), (ii), or (iii);

(c) a variant of the polypeptide having an amino acid sequence of SEQ ID NO. 2 comprising a substitution, deletion, and/or insertion of one or more amino acids;

(d) an allelic variant of (a) or (b); and (e) a fragment of (a), (b), or (d) that has acid phosphatase activity.

The present invention also relates to isolated nucleic acid sequences encoding the polypeptides and to nucleic acid constructs, vectors, and host cells comprising the nucleic acid sequences as well as methods for producing and using the polypeptides.

BRIEF DESCRIPTION OF THE FIGURES

FIG. 1 shows the genomic DNA sequence and the deduced amino acid sequence of a *Fusarium venenatum* phospholipase (SEQ ID NOS. 1 and 2, respectively).

DETAILED DESCRIPTION OF THE INVENTION

Polypeptides Having Acid Phosphatase Activity

Figure 2:
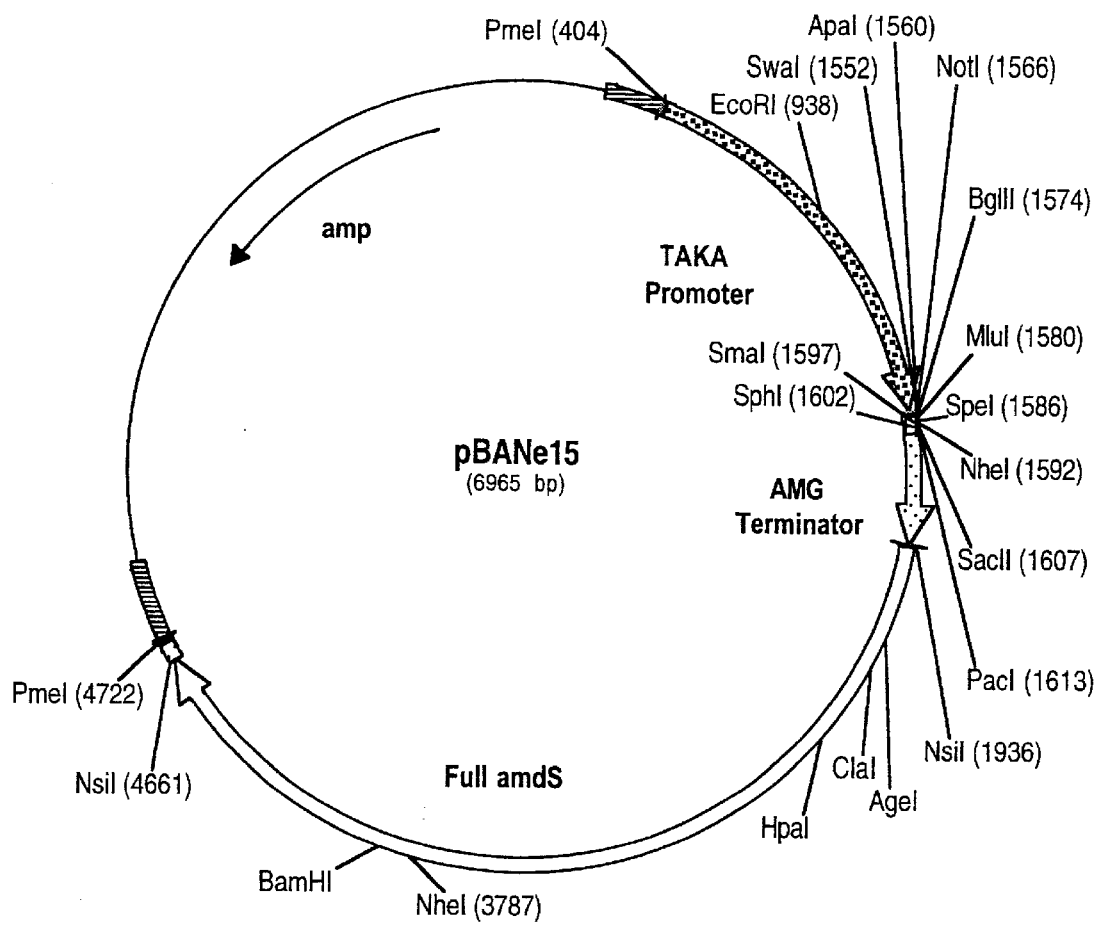
FIG. 2 shows a restriction map of pBANE15.

The term "acid phosphatase activity" is defined herein as an orthophosphoric-ester phosphohydrolase activity which catalyzes the hydrolysis of an orthophosphate monoester to an alcohol and orthophosphate. Natural substrates include, but are not limited to, ATP, ADP, AMP, phosphoenolpyruvate, phosphothreonine, pyridoxal 5'-phosphate, FMN, and hexose phosphates, e.g., myoinositol hexakis-phosphate. For purposes of the present invention, acid phosphatase activity is determined according to the procedure described by Roche® Reagents for Acid Phosphatase (Roche Diagnostic Systems, Summerville, N.J.) where the release of α-naphthol from 3 mM α-naphthylphosphate catalyzed by the polypeptide having acid phosphatase activity at 37° C., pH 4.5 in 0.1 M sodium acetate buffer is measured by coupling the liberated α-naphthol to 1 mM diazotized 2-amino-5-chlorotoluene (Fast Red TR) to produce a diazo dye. The formation of the diazo dye is measured at 405 nm. One unit of acid phosphatase activity is defined as the amount of acid phosphatase activity which converts 1.0 μmole of α-naphthylphosphate to 1.0 μmole of α-naphthol per minute per liter of sample with the concomitant production of 1.0 μmole of diazo dye at 37° C., pH 4.5.

In a first embodiment, the present invention relates to isolated polypeptides having an amino acid sequence which has a degree of identity to amino acids 19 to 318 of SEQ ID NO. 2 (i.e., the mature polypeptide) of at least about 65%, preferably at least about 70%, more preferably at least about 80%, even more preferably at least about 90%, most preferably at least about 95%, and even most preferably at least about 97%, which have acid phosphatase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from amino acids 19 to 318 of SEQ ID NO. 2. For purposes of the present invention, the degree of identity between two amino acid sequences is determined by the Clustal method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5.

Preferably, the polypeptides of the present invention comprise the amino acid sequence of SEQ ID NO. 2 or an allelic variant thereof; or a fragment thereof that has acid phosphatase activity. In a more preferred embodiment, the polypeptide of the present invention comprises the amino acid sequence of SEQ ID NO. 2. In another preferred embodiment, the polypeptide of the present invention comprises amino acids 19 to 318 of SEQ ID NO. 2, or an allelic variant thereof; or a fragment thereof that has acid phosphatase activity. In another preferred embodiment, the polypeptide of the present invention comprises amino acids 19 to 318 of SEQ ID NO. 2. In another preferred embodiment, the polypeptide of the present invention consists of the amino acid sequence of SEQ ID NO. 2 or an allelic variant thereof; or a fragment thereof that has acid phosphatase activity. In another preferred embodiment, the polypeptide of the present invention consists of the amino acid sequence of SEQ ID NO. 2. In another preferred embodiment, the polypeptide consists of amino acids 19 to 318 of SEQ ID NO. 2 or an allelic variant thereof; or a fragment thereof that has acid phosphatase activity. In another preferred embodiment, the polypeptide consists of amino acids 19 to 318 of SEQ ID NO. 2.

A fragment of SEQ ID NO. 2 is a polypeptide having one or more amino acids deleted from the amino and/or carboxyl terminus of this amino acid sequence. Preferably, a fragment contains at least 240 amino acid residues, more preferably at least 260 amino acid residues, and most preferably at least 280 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

In a second embodiment, the present invention relates to isolated polypeptides having acid phosphatase activity that are encoded by nucleic acid sequences which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with (i) nucleotides 138 to 1252 of SEQ ID NO. 1, (ii) the cDNA sequence contained in nucleotides 138 to 1252 of SEQ ID NO. 1, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual*, 2d edition, Cold Spring Harbor, N.Y.). The subsequence of SEQ ID NO. 1 may be at least 100 nucleotides or preferably at least 200 nucleotides. The subsequences are preferably contiguous sequences. Moreover, the subsequence may encode a polypeptide fragment which has acid phosphatase activity. The polypeptides may also be allelic variants or fragments of the polypeptides that have acid phosphatase activity.

The nucleic acid sequence of SEQ ID NO. 1 or a subsequence thereof, as well as the amino acid sequence of SEQ ID NO. 2 or a fragment thereof, may be used to design a nucleic acid probe to identify and clone DNA encoding polypeptides having acid phosphatase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}$P, $^3$H, $^{35}$S, biotin, or avidin). Such probes are encompassed by the present invention.

Thus, a genomic DNA or cDNA library prepared from such other organisms may be screened for DNA which hybridizes with the probes described above and which encodes a polypeptide having acid phosphatase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO. 1 or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO. 1, its complementary strand, or a subsequence thereof, under very low to very high stringency conditions. Molecules to which the nucleic acid probe hybridizes under these conditions are detected using X-ray film.

In a preferred embodiment, the nucleic acid probe is a nucleic acid sequence which encodes the polypeptide of SEQ ID NO. 2, or a subsequence thereof. In another preferred embodiment, the nucleic acid probe is SEQ ID NO. 1. In another preferred embodiment, the nucleic acid probe is the mature polypeptide coding region of SEQ ID NO. 1. In another preferred embodiment, the nucleic acid probe is the nucleic acid sequence contained in plasmid pDSY170 which is contained in *Escherichia coli* NRRL B-30064, wherein the nucleic acid sequence encodes a polypeptide having acid phosphatase activity. In another preferred embodiment, the nucleic acid probe is the mature polypeptide coding region contained in plasmid pDSY170 which is contained in *Escherichia coli* NRRL B-30064.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third embodiment, the present invention relates to variants of the polypeptide having an amino acid sequence of SEQ ID NO. 2 comprising a substitution, deletion, and/or insertion of one or more amino acids.

The amino acid sequences of the variant polypeptides may differ from the amino acid sequence of SEQ ID NO. 2 or the mature polypeptide thereof by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, LeuNal, Ala/Glu, and Asp/Gly as well as these in reverse.

In a fourth embodiment, the present invention relates to isolated polypeptides having immunochemical identity or partial immunochemical identity to the polypeptide having the amino acid sequence of SEQ ID NO. 2 or the mature polypeptide thereof. The immunochemical properties are determined by immunological cross-reaction identity tests by the well-known Ouchterlony double immunodiffusion procedure. Specifically, an antiserum containing polyclonal antibodies which are immunoreactive or bind to epitopes of the polypeptide having the amino acid sequence of SEQ ID NO. 2 or the mature polypeptide thereof are prepared by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31). A polypeptide having immunochemical identity is a polypeptide which reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Krøll, In N. H. Axelsen, J. Krøll, and B. Weeks, editors, *A Manual of Quantitative Immunoelectrophoresis*, Blackwell Scientific Publications, 1973, Chapter 10. A polypeptide having partial immunochemical identity is a polypeptide which reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11.

The antibody may also be a monoclonal antibody. Monoclonal antibodies may be prepared and used, e.g., according to the methods of E. Harlow and D. Lane, editors, 1988, *Antibodies, A Laboratory Manual*, Cold Spring Harbor Press, Cold Spring Harbor, N.Y.

The polypeptides of the present invention have at least 20%, preferably at least 40%, more preferably at least 60%, even more preferably at least 80%, even more preferably at least 90%, and most preferably at least 100% of the acid phosphatase activity of the mature polypeptide of SEQ ID NO. 2.

A polypeptide of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted. In a preferred embodiment, the polypeptide is secreted extracellularly.

A polypeptide of the present invention may be a bacterial polypeptide. For example, the polypeptide may be a gram positive bacterial polypeptide such as a *Bacillus* polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, or *Bacillus thuringiensis* polypeptide; or a *Streptomyces* polypeptide, e.g., a *Streptomyces lividans* or *Streptomyces murinus* polypeptide; or a gram negative bacterial polypeptide, e.g., an *E. coli* or a *Pseudomonas* sp. polypeptide.

A polypeptide of the present invention may be a fungal polypeptide, and more preferably a yeast polypeptide such as a Candida, Kluyveromyces, Pichia, Saccharomyces, Schizosaccharomyces, or Yarrowia polypeptide; or more preferably a filamentous fungal polypeptide such as an Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium, or Trichoderma polypeptide.

In a preferred embodiment, the polypeptide is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* polypeptide.

In another preferred embodiment, the polypeptide is an *Aspergillus aculeatus, Aspergillus awamori, Aspergillus foetidus, Aspergillus japonicus, Aspergillus nidulans, Aspergillus niger, Aspergillus oryzae, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* polypeptide.

In another preferred embodiment, the polypeptide is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* polypeptide.

In a more preferred embodiment, the *Fusarium venenatum* cell is *Fusarium venenatum* A3/5, which was originally deposited as *Fusarium graminearum* ATCC 20334 and recently reclassified as *Fusarium venenatum* by Yoder and Christianson, 1998, *Fungal Genetics and Biology* 23: 62–80 and O'Donnell et al., 1998, *Fungal Genetics and Biology* 23: 57–67; as well as taxonomic equivalents of *Fusarium venenatum* regardless of the species name by which they are currently known. In another preferred embodiment, the *Fusarium venenatum* cell is a morphological mutant of *Fusarium venenatum* A3/5 or *Fusarium venenatum* ATCC 20334, as disclosed in WO 97/26330.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents. For example, taxonomic equivalents of Fusarium are defined by D. L. Hawksworth, P. M. Kirk, B. C. Sutton, and D. N. Pegler (editors), 1995, In Ainsworth & Bisby's *Dictionary of the Fungi*, Eighth Edition, CAB International, University Press, Cambridge, England, pp. 173–174.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

As defined herein, an "isolated" polypeptide is a polypeptide which is essentially free of other non-acid phosphatase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Nucleic Acid Sequences

The present invention also relates to isolated nucleic acid sequences which encode a polypeptide of the present invention. In a preferred embodiment, the nucleic acid sequence is set forth in SEQ ID NO. 1. In another more preferred embodiment, the nucleic acid sequence is the sequence contained in plasmid pDSY170 that is contained in *Escherichia coli* NRRL B-30064. In another preferred embodiment, the nucleic acid sequence is the mature polypeptide coding region of SEQ ID NO. 1. In another more preferred embodiment, the nucleic acid sequence is the mature polypeptide coding region contained in plasmid pDSY170 that is contained in *Escherichia coli* NRRL B-30064. The present invention also encompasses nucleic acid sequences which encode a polypeptide having the amino acid sequence of SEQ ID NO. 2 or the mature polypeptide thereof, which differ from SEQ ID NO. 1 by virtue of the degeneracy of the genetic code. The present invention also relates to subsequences of SEQ ID NO. 1 which encode fragments of SEQ ID NO. 2 that have acid phosphatase activity.

A subsequence of SEQ ID NO. 1 is a nucleic acid sequence encompassed by SEQ ID NO. 1 except that one or more nucleotides from the 5' and/or 3' end have been deleted. Preferably, a subsequence contains at least 720 nucleotides, more preferably at least 780 nucleotides, and most preferably at least 840 nucleotides.

The present invention also relates to mutant nucleic acid sequences comprising at least one mutation in the mature polypeptide coding sequence of SEQ ID NO. 1, in which the mutant nucleic acid sequence encodes a polypeptide which consists of amino acids 19 to 318 of SEQ ID NO. 2.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Fusarium, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a degree of homology to the mature polypeptide coding sequence of SEQ ID NO. 1 (i.e., nucleotides 138 to 1252) of at least about 65%, preferably about 70%, preferably about 80%, more preferably about 90%, even more preferably about 95%, and most preferably about 97% homology, which encode an active polypeptide. For purposes of the present invention, the degree of homology between two nucleic acid sequences is determined by the Wilbur-Lipman method (Wilbur and Lipman, 1983, *Proceedings of the National Academy of Science USA* 80: 726–730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=3, gap penalty=3, and windows=20.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, themostability, pH optimum, or the like. The variant sequence may be constructed on the basis of the nucleic acid sequence presented as the polypeptide encoding part of SEQ ID NO. 1, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for acid phosphatase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

The present invention also relates to isolated nucleic acid sequences encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with the nucleic acid sequence of SEQ ID NO. 1 or its complementary strand; or allelic variants and subsequences thereof (Sambrook et al., 1989, supra), as defined herein.

The present invention also relates to isolated nucleic acid sequences produced by (a) hybridizing a DNA under very low, low, medium, medium-high, high, or very high stringency conditions with (i) nucleotides 138 to 1252 of SEQ ID NO. 1, (ii) the cDNA sequence contained in nucleotides 138 to 1252 of SEQ ID NO. 1, (iii) a subsequence of (i) or (ii), or (iv) a complementary strand of (i), (ii), or (iii); and (b) isolating the nucleic acid sequence. The subsequence is preferably a sequence of at least 100 nucleotides such as a sequence which encodes a polypeptide fragment which has acid phosphatase activity.

Methods for Producing Mutant Nucleic Acid Sequences

The present invention further relates to methods for producing a mutant nucleic acid sequence, comprising introducing at least one mutation into the mature polypeptide coding sequence of SEQ ID NO. 1 or a subsequence thereof, wherein the mutant nucleic acid sequence encodes a polypeptide which consists of amino acids 19 to 318 of SEQ ID NO. 2 or a fragment thereof which has acid phosphatase activity.

The introduction of a mutation into the nucleic acid sequence to exchange one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of the present invention. The term "coding sequence" is defined herein as a nucleic acid sequence which directly specifies the amino acid sequence of its protein product. The boundaries of a genomic coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in Scientific American, 1980, 242: 74–94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423–488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for Bacillus NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109–137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

In a preferred embodiment, the signal peptide coding region is nucleotides 84 to 137 of SEQ ID NO. 1 which encodes amino acids 1 to 18 of SEQ ID NO. 2.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

The present invention also relates to nucleic acid constructs for altering the expression of an endogenous gene encoding a polypeptide of the present invention. The constructs may contain the minimal number of components necessary for altering expression of the endogenous gene. In one embodiment, the nucleic acid constructs preferably contain (a) a targeting sequence, (b) a regulatory sequence, (c) an exon, and (d) a splice-donor site. Upon introduction of the nucleic acid construct into a cell, the construct inserts by homologous recombination into the cellular genome at the endogenous gene site. The targeting sequence directs the integration of elements (a)–(d) into the endogenous gene such that elements (b)–(d) are operably linked to the endogenous gene. In another embodiment, the nucleic acid constructs contain (a) a targeting sequence, (b) a regulatory sequence, (c) an exon, (d) a splice-donor site, (e) an intron, and (f) a splice-acceptor site, wherein the targeting sequence directs the integration of elements (a)–(f) such that elements (b)–(f) are operably linked to the endogenous gene. However, the constructs may contain additional components such as a selectable marker.

In both embodiments, the introduction of these components results in production of a new transcription unit in which expression of the endogenous gene is altered. In essence, the new transcription unit is a fusion product of the sequences introduced by the targeting constructs and the endogenous gene. In one embodiment in which the endogenous gene is altered, the gene is activated. In this embodiment, homologous recombination is used to replace, disrupt, or disable the regulatory region normally associated with the endogenous gene of a parent cell through the insertion of a regulatory sequence which causes the gene to be expressed at higher levels than evident in the corresponding parent cell. The activated gene can be further amplified by the inclusion of an amplifiable selectable marker gene in the construct using methods well known in the art (see, for example, U.S. Pat. No. 5,641,670). In another embodiment in which the endogenous gene is altered, expression of the gene is reduced.

The targeting sequence can be within the endogenous gene, immediately adjacent to the gene, within an upstream gene, or upstream of and at a distance from the endogenous gene. One or more targeting sequences can be used. For example, a circular plasmid or DNA fragment preferably employs a single targeting sequence, while a linear plasmid or DNA fragment preferably employs two targeting sequences.

The regulatory sequence of the construct can be comprised of one or more promoters, enhancers, scaffold-attachment regions or matrix attachment sites, negative regulatory elements, transcription binding sites, or combinations of these sequences.

The constructs further contain one or more exons of the endogenous gene. An exon is defined as a DNA sequence which is copied into RNA and is present in a mature mRNA molecule such that the exon sequence is in-frame with the coding region of the endogenous gene. The exons can, optionally, contain DNA which encodes one or more amino acids and/or partially encodes an amino acid. Alternatively, the exon contains DNA which corresponds to a 5' non-encoding region. Where the exogenous exon or exons encode one or more amino acids and/or a portion of an amino acid, the nucleic acid construct is designed such that, upon transcription and splicing, the reading frame is in-frame with the coding region of the endogenous gene so that the appropriate reading frame of the portion of the mRNA derived from the second exon is unchanged.

The splice-donor site of the constructs directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. A splice-acceptor site, like a splice-donor site, is a sequence which directs the splicing of one exon to another exon.

Acting in conjunction with a splice-donor site, the splicing apparatus uses a splice-acceptor site to effect the removal of an intron.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from Bacillus subtilis or Bacillus licheniformis, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an Aspergillus cell are the amdS and pyrG genes of Aspergillus nidulans or Aspergillus oryzae and the bar gene of Streptomyces hygroscopicus.

The vectors of the present invention preferably contain an element(s) that permits integration of the vector into the host cell's genome or autonomous replication of the vector in the cell independent of the genome.

For integration into the host cell genome, the vector may rely on the nucleic acid sequence encoding the polypeptide or any other element of the vector for integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location (s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in Bacillus. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a Streptomyces cell, e.g., *Streptomyces lividans* and *Streptomyces murinus*, or gram negative bacteria such as *E. coli* and Pseudomonas sp. In a preferred embodiment, the bacterial host cell is a *Bacillus lentus, Bacillus licheniformis, Bacillus stearothermophilus*, or *Bacillus subtilis* cell. In another preferred embodiment, the Bacillus cell is an alkalophilic Bacillus.

The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred embodiment, the yeast host cell is a Candida, Hansenula, Kluyveromyces, Pichia, Saccharomyces, Schizosaccharomyces, or Yarrowia cell.

In a most preferred embodiment, the yeast host cell is a Saccharomyces carlsbergensis, Saccharomyces cerevisiae, Saccharomyces diastaticus, Saccharomyces douglasii, Saccharomyces kluyveri, Saccharomyces norbensisor *Saccharomyces oviformis* cell. In another most preferred embodiment, the yeast host cell is a *Kluyveromyces lactis* cell. In another most preferred embodiment, the yeast host cell is a Yarrowia lipolytica cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, or Trichoderma.

In a most preferred embodiment, the filamentous fungal host cell is an *Aspergillus awarmori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor*

*miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. Suitable methods for transforming Fusarium species are described by Malardier et al., 1989, *Gene* 78: 147–156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a strain, which in its wild-type form is capable of producing the polypeptide, to produce a supernatant comprising the polypeptide; and (b) recovering the polypeptide. Preferably, the strain is of the genus Fusarium, and more preferably *Fusarium venenatum*.

The present invention also relates to methods for producing a polypeptide of the present invention comprising (a) cultivating a host cell under conditions conducive for production of the polypeptide; and (b) recovering the polypeptide.

The present invention also relates to methods for producing a polypeptide of the present invention comprising (a) cultivating a host cell under conditions conducive for production of the polypeptide, wherein the host cell comprises a mutant nucleic acid sequence having at least one mutation in the mature polypeptide coding region of SEQ ID NO. 1, wherein the mutant nucleic acid sequence encodes a polypeptide which consists of amino acids 19 to 318 of SEQ ID NO. 2, and (b) recovering the polypeptide.

The present invention further relates to methods for producing a polypeptide of the present invention comprising (a) cultivating a homologously recombinant cell, having incorporated therein a new transcription unit comprising a regulatory sequence, an exon, and/or a splice donor site operably linked to a second exon of an endogenous nucleic acid sequence encoding the polypeptide, under conditions conducive for production of the polypeptide; and (b) recovering the polypeptide. The methods are based on the use of gene activation technology, for example, as described in U.S. Pat. No. 5,641,670.

In the production methods of the present invention, the cells are cultivated in a nutrient medium suitable for production of the polypeptide using methods known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Plants

The present invention also relates to a transgenic plant, plant part, or plant cell which has been transformed with a nucleic acid sequence encoding a polypeptide having acid phosphatase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as festuca, lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, *Cell* 21: 285–294). Organ-specific promoters may be, for example, a promoter from storage sink tissues such as seeds, potato tubers, and fruits (Edwards & Coruzzi, 1990, *Ann. Rev. Genet.* 24: 275–303), or from metabolic sink tissues such as meristems (Ito et al., 1994, *Plant Mol. Biol.* 24: 863–878), a seed specific promoter such as the glutelin, prolamin, globulin, or albumin promoter from rice (Wu et al., 1998, *Plant and Cell Physiology* 39: 885–889), a *Vicia faba* promoter from the legumin B4 and the unknown seed protein gene from *Vicia faba* (Conrad et al., 1998, *Journal of Plant Physiology* 152: 708–711), a promoter from a seed oil body protein (Chen et al., 1998, Plant and Cell Physiology 39: 935–941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991–1000, the chlorella virus adenine methyltransferase gene promoter (Mitra and Higgins, 1994, *Plant Molecular Biology* 26: 85–93), or the aldP gene promoter from rice (Kagaya et al., 1995, *Molecular and General Genetics* 248: 668–674), or a wound inducible promoter such as the potato pin2 promoter (Xu et al., 1993, *Plant Molecular Biology* 22: 573–588).

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including Agrobacterium-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15–38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275–281; Shimamoto, 1994, *Current Opinion Biotechnology* 5: 158–162; Vasil et al., 1992, *Bio/Technology* 10: 667–674). An alternative method for transformation of monocots is based on protoplast transformation as described by Omirulleh et al., 1993, *Plant Molecular Biology* 21: 415–428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a polypeptide having acid phosphatase activity of the present invention under conditions conducive for production of the polypeptide; and (b) recovering the polypeptide.

Removal or Reduction of Acid Phosphatase Activity

The present invention also relates to methods for producing a mutant cell of a parent cell, which comprises disrupting or deleting a nucleic acid sequence encoding the polypeptide or a control sequence thereof, which results in the mutant cell producing less of the polypeptide than the parent cell when cultivated under the same conditions.

The construction of strains which have reduced acid phosphatase activity may be conveniently accomplished by modification or inactivation of a nucleic acid sequence necessary for expression of the polypeptide having acid phosphatase activity in the cell. The nucleic acid sequence to be modified or inactivated may be, for example, a nucleic acid sequence encoding the polypeptide or a part thereof essential for exhibiting acid phosphatase activity, or the nucleic acid sequence may have a regulatory function required for the expression of the polypeptide from the coding sequence of the nucleic acid sequence. An example of such a regulatory or control sequence may be a promoter sequence or a functional part thereof, i.e., a part which is sufficient for affecting expression of the polypeptide. Other control sequences for possible modification are described above.

Modification or inactivation of the nucleic acid sequence may be performed by subjecting the cell to mutagenesis and selecting or screening for cells in which the acid phosphatase producing capability has been reduced. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the cell to be mutagenized in the presence of the mutagenizing agent of choice under suitable conditions, and selecting for cells exhibiting reduced acid phosphatase activity or production.

Modification or inactivation of production of a polypeptide of the present invention may be accomplished by introduction, substitution, or removal of one or more nucleotides in the nucleic acid sequence encoding the polypeptide or a regulatory element required for the transcription or translation thereof. For example, nucleotides may be inserted or removed so as to result in the introduction of a stop cod on, the removal of the start codon, or a change of the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleic acid sequence to be modified, it is preferred that the modification be performed in vitro as exemplified below.

An example of a convenient way to eliminate or reduce production by a host cell of choice is by gene replacement or gene interruption. In the gene interruption method, a nucleic acid sequence corresponding to the endogenous gene or gene fragment of interest is mutagenized in vitro to produce a defective nucleic acid sequence which is then transformed into the host cell to produce a defective gene. By homologous recombination, the defective nucleic acid sequence replaces the endogenous gene or gene fragment. It may be desirable that the defective gene or gene fragment also encodes a marker which may be used for selection of transformants in which the gene encoding the polypeptide has been modified or destroyed.

Alternatively, modification or inactivation of the nucleic acid sequence may be performed by established anti-sense techniques using a nucleotide sequence complementary to the polypeptide encoding sequence. More specifically, production of the polypeptide by a cell may be reduced or eliminated by introducing a nucleotide sequence complementary to the nucleic acid sequence encoding the polypeptide which may be transcribed in the cell and is capable of hybridizing to the polypeptide mRNA produced in the cell. Under conditions allowing the complementary anti-sense nucleotide sequence to hybridize to the polypeptide mRNA, the amount of polypeptide translated is thus reduced or eliminated.

It is preferred that the cell to be modified in accordance with the methods of the present invention is of microbial origin, for example, a fungal strain which is suitable for the production of desired protein products, either homologous or heterologous to the cell.

The present invention further relates to a mutant cell of a parent cell which comprises a disruption or deletion of a nucleic acid sequence encoding the polypeptide or a control sequence thereof, which results in the mutant cell producing less of the polypeptide than the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of acid phosphatase activity by fermentation of a cell which produces both a polypeptide of the present invention as well as the protein product of interest by adding an effective amount of an agent capable of inhibiting acid phosphatase activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of acid phosphatase activity by cultivating the cell under conditions permitting the expression of the product, subjecting the resultant culture broth to a combined pH and temperature treatment so as to reduce the acid phosphatase activity substantially, and recovering the product from the culture broth. Alternatively, the combined pH and temperature treatment may be performed on an enzyme preparation recovered from the culture broth. The combined pH and temperature treatment may optionally be used in combination with a treatment with a acid phosphatase inhibitor.

In accordance with this aspect of the invention, it is possible to remove at least 60%, preferably at least 75%, more preferably at least 85%, still more preferably at least 95%, and most preferably at least 99% of the acid phosphatase activity. Complete removal of acid phosphatase activity may be obtained by use of this method.

The combined pH and temperature treatment is preferably carried out at a pH in the range of 6.5–7 and a temperature in the range of 40–70° C. for a sufficient period of time to attain the desired effect, where typically, 30 to 60 minutes is sufficient.

The methods used for cultivation and purification of the product of interest may be performed by methods known in the art.

The methods of the present invention for producing an essentially acid phosphatase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The acid phosphatase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from acid phosphatase activity which is produced by a method of the present invention.

Compositions

In a still further aspect, the present invention relates to compositions comprising a polypeptide of the present invention. Preferably, the compositions are enriched in a polypeptide of the present invention. In the present context, the term "enriched" indicates that the acid phosphatase activity of the composition has been increased, e.g., with an enrichment factor of 1.1.

The composition may comprise a polypeptide of the invention as the major enzymatic component, e.g., a monocomponent composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be producible by means of a microorganism belonging to the genus Aspergillus, preferably *Aspergillus aculeatus, Aspergillus awamori, Aspergillus niger*, or *Aspergillus oryzae*, or Trichoderma, Humicola, preferably *Humicola insolens*, or Fusarium, preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporun , Fusarium reticulatum, Fusarium roseum, Fusarium sambucinum, Fusarium sarcochroum, Fusarium sulphureum, Fusarium toruloseum, Fusarium trichothecioides*, or *Fusarium venenatum*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having acid phosphatase activity.

A polypeptide of the present invention may be used for preparing nucleoside 5'-phosphates according to procedures known in the art. See, for example, EP 857788.

A polypeptide of the present invention may also be used in combination with a phytase to hydrolyze phytate in food, feed, and fodder products according to procedures known in the art. See, for example, U.S. Pat. Nos. 5,443,979 and 5,554,399.

Signal Peptide

The present invention also relates to nucleic acid constructs comprising a gene encoding a protein operably linked to one or both of a first nucleic acid sequence consisting of nucleotides 84 to 137 of SEQ ID NO. 1 encoding a signal peptide consisting of amino acids 1 to 18 of SEQ ID NO. 2, wherein the gene is foreign to the nucleic acid sequence.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The nucleic acid sequence encoding the signal peptide may be operably linked to foreign genes with other control sequences. Such other control sequences are described supra.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred embodiment, the protein is an oxidoreductase, transferase, hydrolase, lyase, isomerase, or ligase. In an even more preferred embodiment, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples which should not be construed as limiting the scope of the invention.

EXAMPLES

Chemicals used as buffers and substrates were commercial products of at least reagent grade.

Media and Solutions

NZY plates were composed per liter of 5 g of NaCl, 2 g of $MgSO_4 \cdot 7H_2O$, 5 g of yeast extract, 10 g of NZ amine, and 15 g of Bacto agar.

AMG trace metals solution was composed per liter of 14.3 g of $ZnSO_4 \cdot 7H_2O$, 2.5 g of $CuSO_4 \cdot 5H_2O$, 0.5 g of $NiCl_2$, 13.8 g of $FeSO_4$, 8.5 g of $MnSO_4$, and 3.0 g of citric acid.

Biotin stock solution was composed of 5 mg of biotin in 100 ml of 50% ethanol:

COVE trace metals solution was composed per liter of 0.04 g of $NaB_4O_7 \cdot 10H_2O$, 0.4 g of $CuSO_4 \cdot 5H_2O$, 1.2 g of $FeSO_4 \cdot 7H_2O$, 0.7 g of $MnSO_4 \cdot H2O$, 0.8 g of $Na_2MoO_2 \cdot 2H_2O$, and 10 g of $ZnSO_4 \cdot 7H_2O$.

50×COVE salts solution was composed per liter of 26 g of KCI, 26 g of $MgSO_4 \cdot 7H_2O$, 76 g of $KH_2PO_4$, and 50 ml of COVE trace metals.

COVE plate medium was composed per liter of 342.3 g of sucrose, 20 ml of 50×COVE salt solution, 10 ml of 1 M acetamide, 10 ml of 1.5 M $CsCl_2$, and 25 g of Noble agar. 50×Vogels medium was composed per liter of 150 g of sodium citrate, 250 g of $KH_2PO_4$, 10 g of $MgSO_4 \cdot 7H_2O$, 10 g of $CaCl_2 \cdot 2H_2O$, 2.5 ml of biotin stock solution, and 5.0 ml of AMG trace metals solution.

COVE top agarose was composed per liter of 20 ml of 50×COVE salts, 0.8 M sucrose, 1.5 M cesium chloride, 1.0 M acetamide, and 10 g of low melt agarose, pH adjusted to 6.0.

RA sporulation medium was composed per liter of 50 g of succinic acid, 12.1 g of $NaNO_3$, 1 g of glucose, 20 ml of 50×Vogels, and 0.5 ml of a 10 mg/ml NaMoO$_4$ stock solution, pH to 6.0.

YEG medium was composed per liter of 5 g of yeast extract and 20 g of glucose.

YEPG medium was composed per liter of 10 g of yeast extract, 20 g of peptone, and 20 g of glucose.

STC was composed of 0.8 M sorbitol, 25 mM Tris pH 8, 25 mM CaCl$_2$.

SPTC was composed of 40% PEG 4000, 0.8 M sorbitol, 25 mM Tris pH 8, 25 mM CaCl$_2$.

M400 medium was composed per liter of 50 g of maltodextrin, 2 g of MgSO$_4$-7H$_2$O, 2 g of KH$_2$PO$_4$, 4 g of citric acid, 8 g of yeast extract, 2 g of urea, 0.5 ml of AMG trace metals solution, and 0.5 g of CaCl$_2$.

TAE buffer was composed per liter of 4.84 g of Tris Base, 1.14 ml of glacial acetic acid, and 2 ml of 0.5 M EDTA pH 8.0.

Example 1

Fermentation and Mycelial Tissue

*Fusarium venenatum* CC1-3, a morphological mutant of Fusarium strain ATCC 20334 (Wiebe et al., 1991, *Mycol. Research* 95: 1284–1288), was grown in a two-liter lab-scale fermentor using a fed-batch fermentation scheme with NUTRIOSE™ (Roquette Freres, S. A., Beinheim, France) as the carbon source and yeast extract. Ammonium phosphate was provided in the feed. The pH was maintained at 6 to 6.5, and the temperature was kept at 30° C. with positive dissolved oxygen.

Mycelial samples were harvested at 2, 4, 6, and 8 days post-inoculum and quick-frozen in liquid nitrogen. The samples were stored at −80° C. until they were disrupted for RNA extraction.

Example 2 cDNA Library Construction

Total cellular RNA was extracted from the mycelial samples described in Example 1 according to the method of Timberlake and Barnard (1981, *Cell* 26: 29–37), and the RNA samples were analyzed by Northern hybridization after blotting from 1% formaldehyde-agarose gels (Davis et al., 1986, *Basic Methods in Molecular Biology*, Elsevier Science Publishing Co., Inc., New York). Polyadenylated mRNA fractions were isolated from total RNA with an mRNA Separator Kit™ (Clontech Laboratories, Inc., Palo Alto, Calif.) according to the manufacturer's instructions. Double-stranded cDNA was synthesized using approximately 5 µg of poly(A)+ mRNA according to the method of Gubler and Hoffman (1983, *Gene* 25: 263–269) except a NotI-(dT)18 primer (Pharmacia Biotech, Inc., Piscataway, N.J.) was used to initiate first strand synthesis. The cDNA was treated with mung bean nuclease (Boehringer Mannheim Corporation, Indianapolis, Ind.) and the ends were made blunt with T4 DNA polymerase (New England Biolabs, Beverly, Mass.).

The cDNA was digested with NotI, size selected by agarose gel electrophoresis (ca. 0.7–4.5 kb), and ligated with pZErO-2.1 (Invitrogen Corporation, Carlsbad, Calif.) which had been cleaved with NotI plus EcoRV and dephosphorylated with calf-intestine alkaline phosphatase (Boehringer Mannheim Corporation, Indianapolis, Ind.). The ligation mixture was used to transform competent *E. coli* TOP10 cells (Invitrogen Corporation, Carlsbad, Calif.). Transformants were selected on 2YT agar plates (Miller, 1992, *A Short Course in Bacterial Genetics. A Laboratory Manual and Handbook for Escherichia coli and Related Bacteria*, Cold Spring Harbor Press, Cold Spring Harbor, N.Y.) which contained kanamycin at a final concentration of 50 µg/ml.

Two independent directional cDNA libraries were constructed using the plasmid cloning vector pZErO-2.1. Library A was made using mRNA from mycelia harvested at four days, and Library B was constructed with mRNA from the six day time point. Neither cDNA library was amplified in order to examine a representative "snapshot" of the gene expression profile in the cells. Instead the libraries were plated, titered, and independent clones from each was analyzed by DNA sequencing.

Library A (4 day cells) consisted about $7.5 \times 10^4$ independent clones and Library B (6 day cells) consisted of roughly $1.2 \times 10^5$ clones. Miniprep DNA was isolated from forty colonies in each library and checked for the presence and size of cDNA inserts. In this analysis 39 of 40 colonies (97.5%) from Library A contained inserts with sizes ranging from 600 bp to 2200 bp (avg.=1050 bp). Similarly, 39 of 40 colonies (97.5%) picked from Library B had inserts with sizes ranging from 800 bp to 3600 bp (avg.=1380 bp).

Example 3

Template Preparation and Nucleotide Sequencing

From each cDNA library described in Example 2, 1192 transformant colonies were picked directly from the transformation plates into 96-well microtiter dishes which contained 200 µl of 2YT broth (Miller, 1992, supra) with 50 µg/ml kanamycin. The plates were incubated overnight at 37° C. without shaking. After incubation 100 µl of sterile 50% glycerol was added to each well. The transformants were replicated into secondary, deep-dish 96-well microculture plates (Advanced Genetic Technologies Corporation, Gaithersburg, Md.) containing 1 ml of Magnificent Broth™ (MacConnell Research, San Diego, Calif.) supplemented with 50 µg of kanamycin per ml in each well. The primary microtiter plates were stored frozen at −80° C. The secondary deep-dish plates were incubated at 37° C. overnight with vigorous agitation (300 rpm) on rotary shaker. To prevent spilling and cross-contamination, and to allow sufficient aeration, each secondary culture plate was covered with a polypropylene pad (Advanced Genetic Technologies Corporation, Gaithersburg, Md.) and a plastic microtiter dish cover.

DNA was isolated from each well using the 96-well Miniprep Kit protocol of Advanced Genetic Technologies Corporation (Gaithersburg, Md.) as modified by Utterback et al. (1995, *Genome Sci. Technol.* 1: 1–8). Single-pass DNA sequencing was done with a Perkin-Elmer Applied Biosystems Model 377 Sequencer XL (Perkin-Elmer Applied Biosystems, Inc., Foster City, Calif.) using dye-terminator chemistry (Giesecke et al., 1992, *Journal of Virology Methods* 38: 47–60) and the reverse lac sequencing primer.

Example 4

Analysis of DNA Sequence Data

Nucleotide sequence data were scrutinized for quality, and samples giving improper spacing or ambiguity levels exceeding 2% were discarded or re-run. Vector sequences were trimmed manually with assistance of FACTURA™ software (Perkin-Elmer Applied Biosystems, Inc., Foster City, Calif.). In addition, sequences were truncated at the end of each sample when the number of ambiguous base calls increased. All sequences were compared to each other to determine multiplicity using AutoAssembler™ software (Perkin-Elmer Applied Biosystems, Inc., Foster City, Calif.). Lastly, all sequences were translated in three frames and searched against a non-redundant database (NRDB) using GeneAssist™ software (Perkin-Elmer Applied Biosystems, Inc., Foster City, Calif.) with a modified Smith-Waterman algorithm using the BLOSUM 62 matrix with a threshold score of 70. The NRDB was assembled from Genpept, Swiss-Prot, and PIR databases.

Example 5

Identification of a Partial Acid Phosphatase cDNA Clone

A putative acid phosphatase clone was identified by partial sequencing of random cDNA clones using an Applied Biosystems Model 377 XL Automated DNA Sequencer according to the manufacturer's instructions and comparison of the deduced amino acid sequence to the amino acid sequence of *Yarrowia lipolytica* acid phosphatase (Swissprot accession number P30887) as described in Example 4. The clone was presumed to be a partial fragment on the basis of its alignment to the *Yarrowia lipolytica* acid phosphatase amino acid sequence. This clone was designated *E. coli* FC0238 containing pFC0238. pFC0238 was selected for use as a probe to screen a *Fusarium venenatum* genomic library.

Example 6

Fusarium venenatum Genomic DNA Extraction

*Fusarium venenatum* CC1-3 was grown for 24 hours at 28° C. and 150 rpm in 25 ml of YEG medium. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia which were subsequently frozen in liquid nitrogen. The frozen mycelia were ground to a fine powder in an electric coffee grinder, and the powder was added to 20 ml of TE buffer and 5 ml of 20% w/v sodium dodecylsulfate (SDS) in a disposable plastic centrifuge tube. The mixture was gently inverted several times to ensure mixing, and extracted twice with an equal volume of phenol:chloroform:isoamyl alcohol (25:24:1 v/v/v). Sodium acetate (3 M solution) was added to give a final concentration of 0.3 M and the nucleic acids were precipitated with 2.5 volumes of ice cold ethanol. The tube was centrifuged at 15,000×g for 30 minutes and the pellet was allowed to air dry for 30 minutes before resuspension in 0.5 ml of TE buffer. DNase-free ribonuclease A was added to a concentration of 100 µg/ml and the mixture was incubated at 37° C. for 30 minutes. Proteinase K (200 µg/ml) was then added and the mixture was incubated an additional hour at 37° C. Finally, the mixture was extracted twice with phenol:chloroform:isoamyl alcohol (25:24:1 v/v/v) before precipitating the DNA with sodium acetate and ethanol according to standard procedures. The DNA pellet was dried under vacuum, resuspended in TE buffer, and stored at 4° C.

Example 7

Genomic DNA Library Construction and Screening

Genomic libraries of *Fusarium venenatum* were constructed in λZipLox according to the manufacturer's instructions (Life Technologies, Gaithersburg, Md.). *Fusarium venenatum* genomic DNA was partially digested with Tsp509I and size-fractionated on 1% agarose gels. DNA fragments migrating in the size range 3–7 kb were excised and eluted from the agarose gel slices using Prep-a-Gene reagents (BioRad, Hercules, Calif.). The eluted DNA fragments were ligated with EcoRI-cleaved and dephosphorylated λZipLox vector arms (Life Technologies, Gaithersburg, Md.), and the ligation mixtures were packaged using commercial packaging extracts (Stratagene, La Jolla, Calif.). *E. coli* Y1090ZL cells were infected with the phage and plated on NZY plates to a density of 7000 plaques per 150 mm Petri plate.

A total of 42,000 plaques from the library was screened by plaque-hybridization (Davis et al., 1980, *Advanced Bacterial Genetics, A Manual for Genetic Engineering*, Cold Spring Harbor Press, Cold Spring Harbor, N.Y.). DNA was transferred to Hybond N+ nitrocellulose circular filters (Amersham, Arlington Heights, Ill.) using standard protocols. The filters were fixed using UV crosslinking and prehybridized at 65 C. in 6×SSPE, 7% SDS. The filters were hybridized with a 331 bp 5' EcoRI-PstI DNA fragment from the acid phosphatase cDNA clone (FC0238) described in Example 5. The DNA fragment was labeled with $\alpha$-$^{35}$P-dCTP using the Prime-IT, Random Primer Labeling Kit (Stratagene, La Jolla, Calif.) according to the manufacturer's instructions. The filters were washed once for 5 minutes at room temperature in 0.2×SSC, 0.1% SDS, twice for 30 minutes at 65° C. in 0.2×SSC, 0.1% SDS, and a final wash for 5 minutes at room temperature in 2×SSC. The filters were exposed to X-ray film and developed.

Plaques, which gave hybridization signals, were purified twice in *E. coli* Y1090ZL cells, and the individual clones were subsequently excised from the λZipLox vector as pZL1-derivatives (D'Alessio et al., 1992, *Focus®* 14: 7). Chromosome "walking" to obtain adjacent DNA sequences was done using homologous Fusarium venenatum probes at high stringency.

Five plaques were identified that hybridized strongly to the Fusarium venenatum acid phosphatase gene probe, and each of the potential clones was subsequently excised from the λZipLox vector as a pZL1-derivative (D'Alessio et al., 1992, supra). Plasmid DNA was isolated from the clones by passage through *E. coli* DH10B cells (Life Technologies, Gaithersburg, Md.) according to the manufacturer's instructions. The plasmids were digested with KpnI to determine if the clones were identical. The sizes of the cloned inserts were determined by agarose gel electrophoresis. From the digests, there appeared to be four classes of clones. The largest insert comprised a DNA segment of approximately 5 kb.

The partial nucleotide sequence of the four clones was determined using the acid phosphatase specific primers below to determine which clones may be full-length:

| | |
|---|---|
| 5'-CCATACGAAACCGCCCAAGTT-3' | (SEQ ID NO. 3) |
| 5'-CCCATCGGTTACGGCGTCAAT-3' | (SEQ ID NO. 4) |

One of the clones, designated *E. coli* DH10B-pDSY170, contained the entire acid phosphatase open reading frame and was chosen for sequence analysis.

Example 8

Nucleotide Sequencing and Characterization of the Fusarium venenatum Acid Phosphatase Genomic DNA from *E. coli* DH10B-pDSY170

DNA sequencing was performed with an Applied Biosystems Model 377 XL Automated DNA Sequencer using dye-terminator chemistry. Contiguous sequences were generated using a transposon insertion strategy (Primer Island Transposition Kit, Perkin-Elmer/Applied Biosystems, Inc., Foster City, Calif.). The acid phosphatase clone from E. coli DH10B-pDSY170 was sequenced to an average redundancy of 5.3.

The acid phosphatase clone encoded an open reading frame of 954 bp encoding a polypeptide of 318 amino acids. The nucleotide sequence (SEQ ID NO. 1) and deduced amino acid sequence (SEQ ID NO. 2) are shown in FIG. 1. The nucleotide sequence was punctuated by four introns. Using the SignalP program (Nielsen et al., 1997, *Protein Engineering* 10: 1–6), a signal peptide of 18 residues was predicted, hence indicating a molecular weight of approximately 32.1 kDa for the secreted acid phosphatase. Thus, the mature acid phosphatase is composed of 300 amino acids.

A comparative alignment of acid phosphatase sequences was undertaken using the Clustal method (Higgins, 1989, *CABIOS* 5: 151–153) using the LASERGENE™ MEGA-LIGN™ software (DNASTAR, Inc., Madison, Wis.) with an identity table and the following multiple alignment parameters: Gap penalty of 10, and gap length penalty of 10. Pairwise alignment parameters were Ktuple=1, gap penalty-3, windows=5, and diagonals=5.

The comparative alignment showed that the Fusarium venenatum acid phosphatase shared regions of identity with the acid phosphatase protein from Yarrowia lipolytica of 35.7% (Swissprot P30887). There were 5 potential N-linked glycosylation sites (Asn-X-Ser/Thr) within Fusarium venenatum acid phosphatase.

Example 9

Construction of Expression Vector pDSY172

The acid phosphatase expression vector pDSY172 for use in an *Aspergillus oryzae* host was constructed as follows. The acid phosphatase coding region was amplified from pDSY170 described in Example 8 using the following pairs of primers:
5'-GCGGATTTAAATGATGCGTCTGTCAACTATCCT CACTGGAGC-3' (SEQ ID NO. 5) and 5'-GCGGTTAATTAATTATTTCCCAATGAACGACGC CACTCG-3' (SEQ ID NO. 6) for ligation into pBANe15 (FIG. 2). The forward primer introduces a SwaI site upstream of the ATG, and the reverse primer introduces a PacI site after the stop codon.

The amplification reaction (50 µl) contained the following components: 0.5 µg of genomic clone pDSY172, 50 pmol of the forward primer, 50 pmol of the reverse primer, 250 µM each of dATP, dCTP, dGTP, and dTTP, 1×Pwo DNA polymerase buffer, and 2.5 units of Hot Star DNA polymerase (Qiagen, Chatsworth, Calif.). The reactions were incubated in a Perkin-Elmer Model 480 Thermal Cycler programmed for 1 cycle at 95° C. for 15 minutes; 25 cycles each at 94° C. for 1 minute, 60° C. for 1 minute, and 72° C. for 1.5 minutes; 1 cycle at 72° C. for 10 minutes; and a soak cycle at room temperature. The reaction products were isolated on a 1% agarose gel (Eastman Kodak, Rochester, N.Y.) where a 1.2 kb product band was excised from the gel and purified using Qiaex II (Qiagen, Chatsworth, Calif.) according to the manufacturer's instructions.

Figure 3:
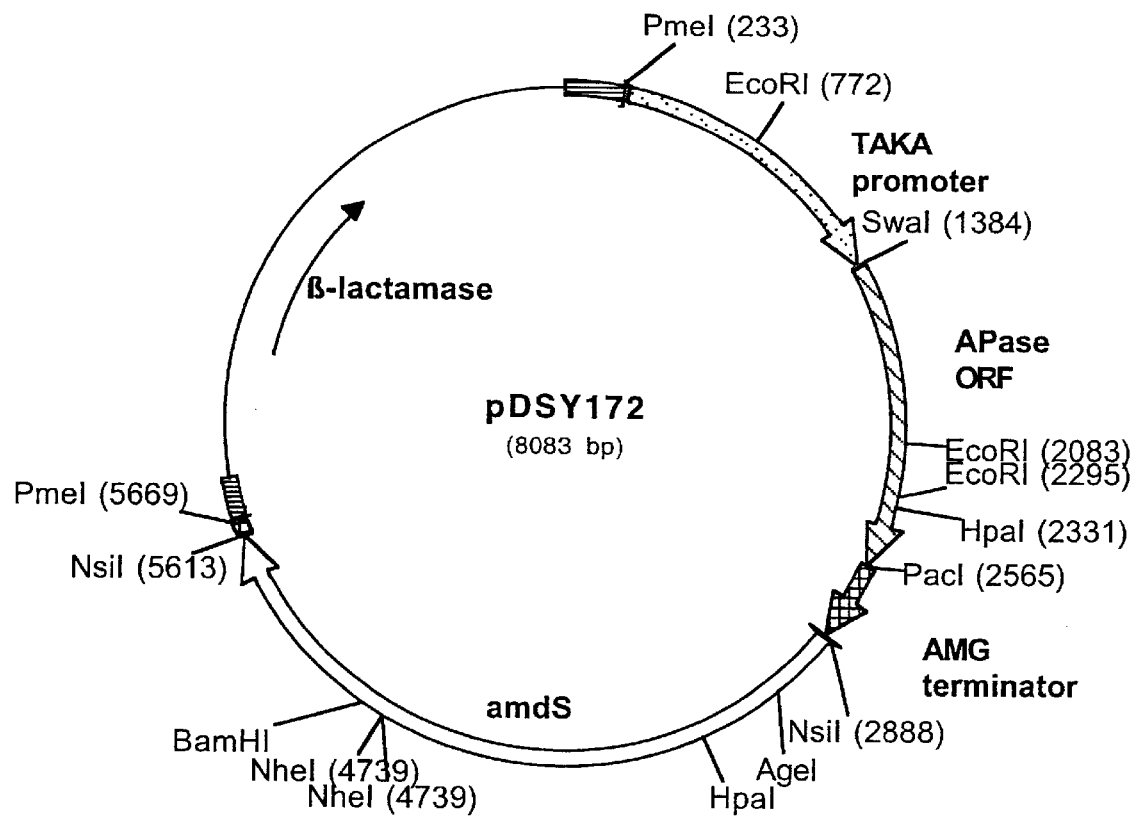
FIG. 3 shows a restriction map of pDSY172.

The amplified acid phosphatase segment was digested with SwaI and PacI, purified by agarose gel electrophoresis using a QiaQuick Spin Column (Qiagen, Chatsworth, Calif.) according to the manufacturer's instructions, and ligated into SwaI/Pac d-digested pBANe15. The resulting expression plasmid was designated as pDSY172 (FIG. 3).

Example 10

Expression of the *Fusarium venenatum* Acid Phosphatase Gene in *Aspergillus oryzae* pDSY172 was transformed into protease-deficient *Aspergillus oryzae* host strain JaL228 (WO 98/12300) using protoplast transformation (Yelton et al., 1984, *Proceedings of the National Academy of Sciences USA* 81: 1470–1474). One hundred µl of protoplasts ($2 \times 10^6$) were placed into a 14 ml Falcon tube with ca. 5 µg of pDSY172 and gently mixed. A 250 µl volume of 60% PEG 4000 in 10 mM Tris-HCl pH 7.5–10 mM $CaCl_2$ was added and mixed by gentle rolling. The tube was then incubated at 37° C. for 30 minutes. Three ml of STC was added and mixed by inversion. The solution was then plated directly onto Cove plates. Plates were incubated 5 days at 37° C. Transformants were transferred to plates of the same medium and incubated 5 days at 37° C. The transformants were purified by streaking spores and picking isolated colonies using the same plates under the same conditions. Twenty-eight *Aspergillus oryzae* JaL228 transformants were recovered.

Spore stocks of each transformant were made with sterile deionized water. A 500 µl volume of each spore stock including the untransformed host was inoculated into 125 ml shake flasks containing 25 ml of MY25 medium. The shake flasks were incubated at 37° C., 200 rpm for 2 days.

Samples of 500 µl were removed at 2 days from each flask. Cells were removed by centrifugation, and 10 µl of each supernatant sample was heated to 95° C. for 5 minutes with an equal volume of SDS-PAGE sample buffer (Novex Experimental Technology, San Diego, Calif.). The denatured supernatant proteins were separated on a 10–20% gradient gel (Novex Experimental Technology, San Diego, Calif.) and stained with Coomassie blue.

Acid phosphatase activity was determined using the procedure described by Roche® Reagents for Acid Phosphatase (Roche Diagnostic Systems, Summerville, N.J.) where the release of a-naphthol from a-naphthylphosphate was measured by coupling the liberated α-naphthol to diazotized 2-amino-5-chlorotoluene (Fast Red TR) to produce a diazo dye. Specifically, a 20 µl sample of the supernatant diluted in 35 µl of 0.1 M sodium acetate pH 4.5 buffer was added to 165 µl of a-naphthylphosphate reagent containing 3 mM α-naphthylphosphate, 1 mM Fast Red TR, 18 mM citric acid, and 54 mM sodium citrate pre-equilibrated to 37° C. in a Cobas Fara II instrument (Roche Diagnostic Systems, Nutley, N.J.). The absorbance at 405 nm was then measured after a 30 second delay for 33 readings every 12 seconds with the following parameters—measurement mode: absorb; reaction mode: PTA; calibrate mode: factor; and decimal point 1. The linear portion of the curve as determined by Kimsearch Calculation Model A (Roche Diagnostic Systems, Nutley, N.J.) was used to calculate the absorbance change per minute. A calculation factor of 969 was used by the Fara software to calculate and report the results in U per liter. The calculation factor of 969 was a result of known constants and represents F in the equation $U/L = (\Delta A/\text{minute[sample]} - \Delta A/\text{minute[reagent blank]})F$. One unit of acid phosphatase activity is defined as the amount of acid phosphatase activity which converts 1.0 µmole of α-naphthylphosphate to 1.0 µmole of α-naphthol per minute per liter of sample with the concomitant production of 1.0 µmole of diazo dye at 37° C., pH 4.5.

The results shown in Table 1 clearly demonstrated the presence of acid phosphatase activity in the samples. SDS-PAGE analysis showed that the acid phosphatase-producing transformants secrete a prominent polypeptide with an apparent molecular weight of approximately 42–45 kDa. The discrepancy between the predicted molecular weight of mature acid phosphatase (ca. 32 kDa) versus that which was observed by SDS-PAGE suggests that the protein is glycosylated. As noted previously, there are 5 potential sites for N-linked glycosylation within the deduced amino acid sequence of *Fusarium venenatum* acid phosphatase.

TABLE 1

Acid phosphatase activity present in culture supernatants from *Aspergillus oryzae*/pDSY17 transformants relative to the highest producer DSY172.19.

| Transformant | Relative activity |
| --- | --- |
| DSY172.01 | 0.11 |
| DSY172.02 | 0.04 |
| DSY172.03 | 0.09 |
| DSY172.04 | 0.13 |
| DSY172.05 | 0.10 |
| DSY172.06 | 0.80 |
| DSY172.07 | 0.29 |
| DSY172.08 | 0.18 |
| DSY172.09 | 0.15 |
| DSY172.10 | 0.04 |
| DSY172.11 | 0.37 |
| DSY172.12 | 0.29 |
| DSY172.13 | 0.07 |
| DSY172.14 | 0.60 |
| DSY172.15 | 0.38 |
| DSY172.16 | 0.08 |
| DSY172.17 | 0.15 |
| DSY172.18 | 0.07 |
| DSY172.19 | 1.0 |
| DSY172.20 | 0.27 |
| DSY172.21 | 0.59 |
| DSY172.22 | 0.07 |
| DSY172.23 | 0.18 |
| DSY172.24 | 0.51 |
| DSY172.25 | 0.60 |
| DSY172.26 | 0.22 |
| DSY172.27 | 0.03 |
| DSY172.28 | 0.05 |
| JaL228 | 0.07 |

Example 11

Construction of Plasmid pSheB1

Figure 4:
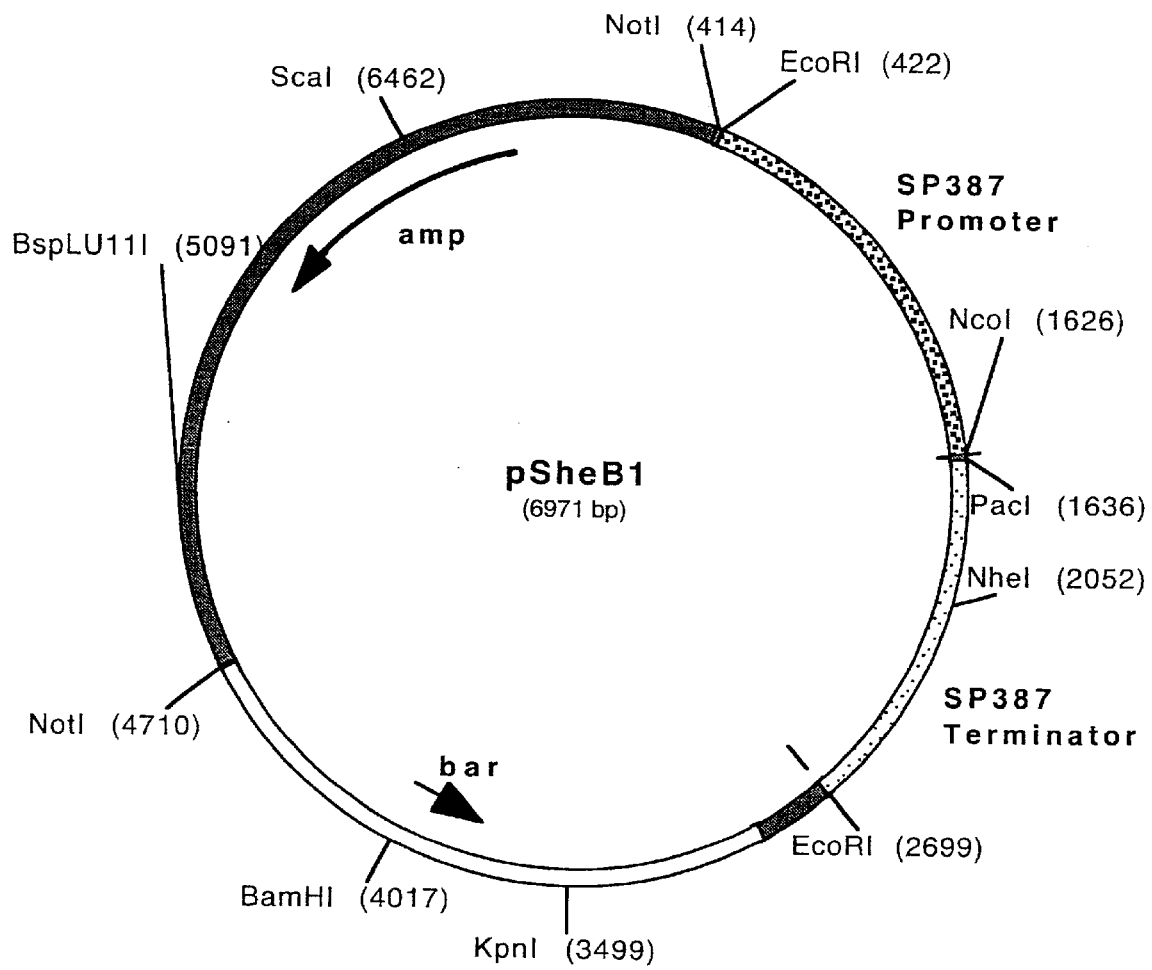
FIG. 4 shows a restriction map of pSheB1.

The *Fusarium venenatum* expression vector pSheB1 (FIG. 4) was generated by modification of pDM181 (WO 98/20136). The modifications included (a) removal of two NcoI sites within the pDM181 sequence, and (b) restoration of the natural translation start of the *Fusariumn oxysporum* trypsin promoter (reconstruction of an NcoI site at the ATG start codon).

Removal of two NcoI sites within the pDM181 sequence was accomplished using the QuikChange™ site-directed mutagenesis kit (Stratagene Cloning Systems, La Jolla, Calif.) according to the manufacturer's instruction with the following pairs of mutagenesis primers:

5'-dCAGTGAATTGGCCTCGATGGCCGCGGCCGCGAATT-3' plus (SEQ ID NO. 7)

5'-dAATTCGCGGCCGCGGCCATCGAGGCC AATTCACTG-3' (SEQ ID NO. 8)

5'-dCACGAAGGAAAGACGATGGCTTTCA CGGTGTCTG-3' plus (SEQ ID NO. 9)

5'-dCAGACACCGTGAAAGCCATCGTCTT TCCTTCGTG-3' (SEQ ID NO. 10)

Restoration of the natural translation start of the *Fusarium oxysporum* trypsin promoter was also accomplished using the Stratagene QuikChange™ site directed mutagenesis kit in conjunction with the following pair of mutagenesis primers:

5'-dCTATCTCTFCACCATGGTACCTTAAT- TAAATACCTTGTTGGAAGCG-3' plus (SEQ ID NO. 11)

5'-dCGCTTCCAACAAGGTATTTAATTAAGG- TACCATGGTGAAGAGATAG-3' (SEQ ID NO. 12)

All site-directed changes were confirmed by DNA sequence analysis of the appropriate vector regions.

Example 12

Construction of Expression Vector pDSY173

The acid phosphatase expression vector pDSY 173 for use in an *Fusarium venenatum* host was constructed as follows. The acid phosphatase coding region was amplified from pDSY170 described in Example 8 using the following pairs of primers: 5'-GCGGTTAATTAATTATTTCCCAATGAACGACGC CACTCG-3' (SEQ ID NO. 13) and 5'-GCGGGCATGCGTCTGTCAACTATCCTCACTG GAGC-3' (SEQ ID NO. 14) for ligation into pSheB1. The forward primer introduces a SphI restriction site at the start codon, and the reverse primer introduces a PacI site after the stop codon.

The amplification reaction (50 µl) contained the following components: 0.5 µg of genomic clone pDSY 170, 50 pmol of the forward primer, 50 pmol of the reverse primer, 250 µM each of dATP, dCTP, dGTP, and dTTP, 1×Pwo DNA polymerase buffer, and 2.5 units of Hot Star DNA polymerase. The reactions were incubated in a Perkin-Elmer Model 480 Thermal Cycler programmed for the same conditions described in Example 9. The reaction products were isolated on a 1% agarose gel where a 1.2 kb product band was excised from the gel and purified using a QiaQuick Spin Column according to the manufacturer's instructions.

Figure 5:
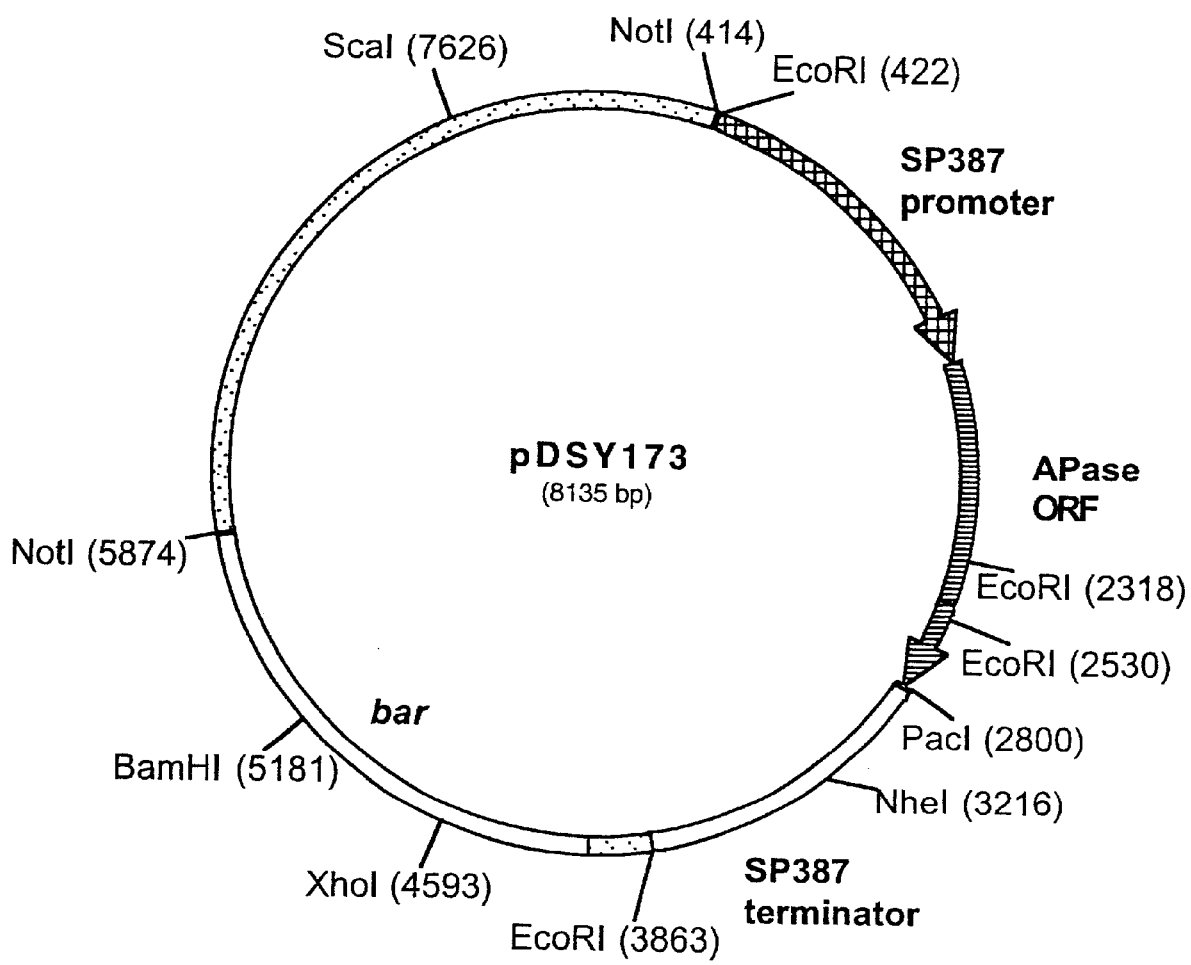
FIG. 5 shows a restriction map of pDSY173.

The amplified acid phosphatase segment was digested with SphI, treated with Klenow to blunt the SphI site and then digested with PacI, purified by agarose gel electrophoresis using a Qiagen Spin Column, and ligated to the vector pSheBI which had been previously cleaved with NcoI, treated with Klenow to blunt the NcoI site and digested with PacI. The blunting of the NcoI and SphI sites in pSheBI and at the acid phosphatase 5' generates upon ligation a C, which is the first base of the second codon in acid phosphatase, at the fourth base in the open reading frame. The resulting expression plasmid was designated as pDSY173 (FIG. 5).

Example 13

Expression of Acid Phosphatase DNA in *Fusarium venenatum*

Spores of *Fusarium venenatum* LyMC1-A (Δtri-5) were generated by inoculating a flask containing 500 ml of RA sporulation medium with 10 plugs from a 1×Vogels medium plate (2.5% Noble agar) supplemented with 2.5% glucose and 2.5 mM sodium nitrate and incubating at 28° C., 150 rpm for 2 to 3 days. Spores were harvested through Miracloth (Calbiochem, San Diego, Calif.) and centrifuged 20 minutes at 7000 rpm in a Sorvall RC-5B centrifuge (E. I. DuPont De Nemours and Co., Wilmington, Del.). Pelleted spores were washed twice with sterile distilled water, resuspended in a small volume of water, aid then counted using a hemocytometer.

Protoplasts were prepared by inoculating 100 ml of YEPG medium with 4×10⁷ spores of *Fusarium venenatum* LyMC1-A and incubating for 16 hours at 24° C. and 150 rpm. The culture was centrifuged for 7 minutes at 3500 rpm in a Sorvall RT 6000D (E. I. DuPont De Nemours and Co., Wilmington, Del.). Pellets were washed twice with 30 ml of 1 M MgSO$_4$ and resuspended in 15 ml of 5 mg/ml of NOVOZYME 234™ (batch PPM 4356, Novo Nordisk A/S, Bagsvaerd, Denmark) in 1 M MgSO$_4$. Cultures were incubated at 24° C. and 150 rpm until protoplasts formed. A volume of 35 ml of 2 M sorbitol was added to the protoplast digest and the mixture was centrifuged at 2500 rpm for 10 minutes. The pellet was resuspended, washed twice with STC, and centrifuged at 2000 rpm for 10 minutes to pellet the protoplasts. Protoplasts were counted with a hemocytometer and resuspended in an 8:2:0.1 solution of STC-:SPTC:DMSO to a final concentration of 1.25×10⁷ protoplasts/ml. The protoplasts were stored at −80° C., after controlled-rate freezing in a Nalgene Cryo 1° C. Freezing Container (VWR Scientific, Inc., San Francisco, Calif.).

Frozen protoplasts of *Fusarium venenatum* LyMC1-A were thawed on ice. The plasmid pDSY173 described in Example 9 was digested with NotI. The digested plasmid was electrophoresed on a 1% agarose gel in TAE buffer and the band containing the 5.4 kb fragment was excised from the gel. The NotI fragment was extracted from the gel slice using a QiaQuick Spin Column according to the manufacturer's instructions. Five µg of the NotI fragment and 5 µl of heparin (5 mg per ml of STC) was added to a 50 ml sterile polypropylene tube. One hundred µl of protoplasts was added, mixed gently, and incubated on ice for 30 minutes. One ml of SPTC was added and incubated 20 minutes at room temperature. After the addition of 25 ml of 40° C. COVE top agarose, the mixture was poured onto an empty 150 mm diameter plate and incubated overnight at room temperature. Then an additional 25 ml of 40° C. COVE top agarose containing 10 mg of BASTA™ per ml was poured on top of the plate and incubated at room temperature for up to 14 days. The active ingredient in the herbicide BASTA™ is phosphinothricin. BASTA™ was obtained from AgrEvo (Hoechst Schering, Rodovre, Denmark) and was extracted twice with phenol:chloroform:isoamyl alcohol (25:24:1), and once with chloroform:isoamyl alcohol (24:1) before use.

Thirty-one transformants were picked directly from the selection plates (COVE underlay with COVE-BASTA™ overlay) into 125 ml shake flasks containing 25 ml of M400 medium and incubated at 28° C., 200 rpm on a platform shaker for 7 days. The untransformed recipient strain was also included as a negative control.

Flasks were sampled at 7 days. Cells were removed by centrifugation, and 10 µl of each supernatant sample was heated to 95° C. for 5 minutes with an equal volume of SDS-PAGE sample buffer (Novex Experimental Technology, San Diego, Calif.). The denatured supernatant proteins were separated on a 10–20% gradient gel (Novex Experimental Technology, San Diego, Calif.) and stained with Coomassie blue.

Acid phosphatase activity in the culture supernatants was also measured using the same assay described in Example 10.

The results shown in Table 2 clearly demonstrated the presence of acid phosphatase activity in the samples. SDS-PAGE analysis showed that the acid phosphatase-producing transformants secrete a prominent polypeptide with an apparent molecular weight of approximately 42–45 kDa where the discrepancy between the predicted molecular weight of mature acid phosphatase (ca. 32 kDa) versus that which was observed by SDS-PAGE suggests that the protein is glycosylated, similar to that observed for the *Aspergillus oryzae* expressed acid phosphatase.

TABLE 2

Acid phosphatase activity present in culture supernatants from *Fusarium venenatum*/pDSY173 transformants relative to the highest producer DSY173.20.

| Transformant | Relative Activity |
| --- | --- |
| DSY173.01 | 0.36 |
| DSY173.02 | 0.71 |
| DSY173.03 | 0.25 |
| DSY173.04 | 0.63 |
| DSY173.05 | 0.40 |
| DSY173.06 | 0.80 |
| DSY173.07 | 0.58 |
| DSY173.08 | 0.32 |
| DSY173.09 | 0.27 |
| DSY173.10 | 0.19 |
| DSY173.11 | 0.16 |
| DSY173.12 | 0.26 |
| DSY173.13 | 0.63 |
| DSY173.14 | 0.44 |
| DSY173.15 | 0.11 |
| DSY173.16 | 0.56 |
| DSY173.17 | 0.47 |
| DSY173.18 | 0.30 |
| DSY173.19 | 0.71 |
| DSY173.20 | 1.0 |
| DSY173.21 | 0.45 |
| DSY173.22 | 0.48 |
| DSY173.23 | 0.82 |
| DSY173.24 | 0.79 |
| DSY173.25 | 0.52 |
| DSY173.26 | 0.88 |
| DSY173.27 | 0.76 |
| DSY173.28 | 0.56 |
| DSY173.29 | 0.49 |
| DSY173.30 | 0.32 |
| DSY173.31 | 0.78 |
| LyMC1A | 0.04 |

Example 14

Purification of Acid Phosphatase Expressed in *Fusarium venenatum*

A 150 ml shake flask broth sample was filtered through Miracloth, centrifuged, and filtered through a 0.45 gm filter. The sample was diluted to 600 ml with distilled water and pH adjusted to 7.0 using 0.1 N HCl. The preparation was loaded onto a Q-Sepharose Big 10 Beads column (Pharmacia Biotech, Inc., Piscataway, N.J.), which contained approximately 80 ml of resin pre-equilibrated with 600 ml of 20 mM sodium phosphate pH 7.0 buffer. The enzyme was eluted with a linear gradient from 20 mM sodium phosphate pH 7.0 to 20 mM sodium phosphate pH 7.0 containing 0.3 M NaCl over 5 column volumes. Acid phosphatase activity was measured by incubating 10 µl of the enzyme sample with 100 i ll of a 2 mg of p-nitrophenyl phosphate solution per ml of 50 mM sodium acetate pH 4.5 buffer. At different time points, the reaction was stopped and color developed by the addition of 100 µl of 1 N NaOH. The absorbance at 405 nm was measured.

The enzyme appeared as three bands on SDS PAGE with molecular weights in the range of approximately 40–50 kDa. After treatment of the sample with endoglycosidase F/N-glycosidase F (Boehringer Mannheim, Indianapolis, Ind.), one band was observed by SDS PAGE with a molecular weight of approximately 32–36 kDa.

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| E. coli DH10B (pDSY170) | NRRL B-30064 | Oct. 27, 1998 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated nucleic acid sequence encoding a polypeptide having acid phosphatase activity, selected from the group consisting of:
    (a) a nucleic acid sequence encoding a polypeptide having an amino acid sequence which has at least 90% identity with amino acids 19 to 318 of SEQ ID NO:2;
    (b) a nucleic acid sequence having at least 90% homology with nucleotides 138 to 1252 of SEQ ID NO:1;
    (c) a nucleic acid sequence which hybridizes under medium-high stringency conditions with (i) nucleotides 138 to 1252 of SEQ ID NO:1, (ii) the cDNA sequence contained in nucleotides 138 to 1252 of SEQ ID NO:1, or (iii) a complementary strand of (i) or (ii), wherein medium-high stringency conditions are defined as prehybridization and hybridization at 42° C. in 5×SSPE, 0.3% SDS, 200 μg/ml sheared and denatured salmon sperm DNA, and 35% formamide, and washes at 60° C. for 15 minutes in 2×SSC, 0.2% SDS; and
    (d) a subsequence of (a), (b), or (c), wherein the subsequence encodes a polypeptide fragment which has acid phosphatase activity.

2. The nucleic acid sequence of claim 1, which encodes a polypeptide having an amino acid sequence which has at least 90% identity with amino acids 19 to 318 of SEQ ID NO:2.

3. The nucleic acid sequence of claim 1, which encodes a polypeptide having an amino acid sequence which has at least 95% identity with amino acids 19 to 318 of SEQ ID NO:2.

4. The nucleic acid sequence of claim 1, which encodes a polypeptide having an amino acid sequence which has at least 97% identity with amino acids 19 to 318 of SEQ ID NO:2.

5. The nucleic acid sequence of claim 1, which encodes a polypeptide comprising the amino acid sequence of SEQ ID NO:2.

6. The nucleic acid sequence of claim 1 which encodes a polypeptide consisting of the amino acid sequence of SEQ ID NO:2, or a fragment thereof which has acid phosphatase activity.

7. The nucleic acid sequence of claim 1 which has at least 90% homology with nucleotides 138 to 1252 of SEQ ID NO:1.

8. The nucleic acid sequence of claim 1 which has at least 95% homology with nucleotides 138 to 1252 of SEQ ID NO:1.

9. The nucleic acid sequence of claim 1 which has at least 97% homology with nucleotides 138 to 1252 of SEQ ID NO:1.

10. The nucleic acid sequence of claim 1, which hybridizes under medium-high stringency with (i) nucleotides 138 to 1252 of SEQ ID NO:1, (ii) the cDNA sequence contained in nucleotides 138 to 1252 of SEQ ID NO:1, or (iii) a complementary strand of (i) or (ii), wherein medium-high stringency conditions are defined as prehybridization and hybridization at 42° C. in 5×SSPE, 0.3% SDS, 200 μg/ml sheared and denatured salmon sperm DNA, and 35% formamide, and washes at 60° C. for 15 minutes in 2×SSC, 0.2% SDS.

11. The nucleic acid sequence of claim 10, which hybridizes under high stringency conditions with (i) nucleotides 138 to 1252 of SEQ ID NO:1, (ii) the cDNA sequence contained in nucleotides 138 to 1252 of SEQ ID NO:1, or (iii) a complementary strand of (i) or (ii), wherein high stringency conditions are defined as prehybridization and hybridization at 42° C. in 5×SSPE, 0.3% SDS, 200 μg/ml sheared and denatured salmon sperm DNA, and 50% formamide, and washes at 65° C. for 15 minutes in 2×SSC, 0.2% SDS; and (b) isolating the nucleic acid sequence.

12. The nucleic acid sequence of claim 1, which is contained in the plasmid pDSY170 which is contained in *Escherichia coli* NRRL B-30064.

13. A nucleic acid construct comprising the nucleic acid sequence of claim 1 operably linked to one or more control sequences which direct the production of the polypeptide in a suitable expression host.

14. A recombinant expression vector comprising the nucleic acid construct of claim 13.

15. A recombinant host cell comprising the nucleic acid construct of claim 13.

16. A method for producing a polypeptide having acid phosphatase activity comprising (a) cultivating the host cell of claim 15 under conditions suitable for production of the polypeptide; and (b) recovering the polypeptide.

17. A nucleic acid construct comprising a gene encoding a protein operably linked to a nucleic acid sequence encoding a signal peptide consisting of nucleotides 84 to 137 of SEQ ID NO:1, wherein the gene is foreign to the nucleic acid sequence.

18. A recombinant expression vector comprising the nucleic acid construct of claim 17.

19. A recombinant host cell comprising the nucleic acid construct of claim 17.

20. A method for producing a protein comprising (a) cultivating the recombinant host cell of claim 19 under conditions suitable for production of the protein; and (b) recovering the protein.

* * * * *

SEQUENCE LISTING

```
<160> NUMBER OF SEQ ID NOS: 14

<210> SEQ ID NO 1
<211> LENGTH: 2544
<212> TYPE: DNA
<213> ORGANISM: Fusarium

<400> SEQUENCE: 1
aattaacttg ttctctggat gtcctccttt gatcttgtcc aaataagctc aattccatca      60
caccataaag gtgtagagtc aagatgcgtc tgtcaactat cctcactgga gcagccctgt     120
tctcgtcctc acaggctctg aacatccttc ttaacaatga tgatggattc ggatctgcga     180
acttgcgtga gatgtaccgt ctcttcaagg aaaagggcca caatggtacc aagcctcctt     240
cattttccca ggaaccaata actgacatac cttgaccagt ctggctcgtt gcaccagcca     300
ccaagcaaag tggcaagggc ggtacctctg atttcaccac cgagggcaat ttgactggac     360
cttctcaata cgatctaatt cccaagggcg caccatcagt atgatcacca agtacacggg     420
tcgcaatgag atgagactaa cagatctttt ttaggtcgga agtgatccaa aggatagcca     480
aatctggtac tacaatggca ctcctgctgc gtgcacattt gttgctctcg actatgttct     540
cccccgatac gccaacttta gcgttcctga ccttgtcgta cgttttgacc cttttgacag     600
accaacattg atacttactt ccttaggtga ctggtcctaa ctatggcacc aacttgggcg     660
gtttcgtatg gactctatcc ggtactgctg gtgctgcgta agtcttcaac acatcgactc     720
agtgaaacgt ataaaatact gacaggactg tagatacgcc gctacaaacc gtggaattcc     780
cgcaattgcc atatcagcga gcaaccagga agttccctac ttcgaactga caaaccgcac     840
caacccagct acgtgggctg cccaagcctc tgtaaaattc gtcgagaact ttatttcgac     900
agctggcaag aacggtcccc ttttgcccat cggktacggc gtcaatgtca atcttcccgt     960
gttgacgaag aaagatcacg accccgaatt cgtgcagacg aggttcacgg gcaatgcgca    1020
cgttaacgaa gcggtgcttg atccgaagaa gggaacgttt acgtgggcca acatcaagcc    1080
ttatgctgcc ggcgtgaatg cttgtatcaa tggcaactgc tcgctgcccg gtgagacgta    1140
tgttgttgag aacggaaagg cgtctgtatc gttttataca gtggattaca gtgctcccga    1200
aactgagtac accgaatcac tcatcgatcg agtggcgtcg ttcattggga aataaacaag    1260
```

-continued

```
aaaggaccag ccccgaagtt ggttggttaa caatgccata gatcataaca gataatgata    1320
gtatacatgt tgttacatga catgatgcgc ctgcttttcc atatgcaatt agaaaatagc    1380
aagttcaata tttctttccc gcgccacctt ctcgatatcg aacgtcgatg tcccgtcttc    1440
ccacgccgcg tcgatcagct caaacatcac cttgatcagc tcaacagtgt cagtcgcgaa    1500
ggattttttg acatcttcca tagtcctttt ccacgtagga tgtagcttta gtagcggaac    1560
ctccagaccg gcgttgatga cgggatacgt caaccgttat gtactaacaa gtgctggtta    1620
cgaggctctt cataggcctt cagaagagca tctattgctg caatgagacg acaaagtaca    1680
acttctgtgc taggaaagtt tttgggtgtt tcgtcgtaca ggtcaataat gccccttgct    1740
tttcgctcca ttctctgacg gcgacgaact tcaagaatgc cagccagcct ccaggactcc    1800
cagaggtgca cgtgtaatga ctcacctatg tcacccggcc atgcccaaaa gcgactctca    1860
gtatactccg gatcgttatc gacgagtcct gcaaatatgt ctagtaatga tcgcgggaca    1920
cccgacacga cttcgatgcc gtcggctcga ccgctctgag tgtcagcttg gagacgacga    1980
aggagcttcc agacgccgat gggtggtttg gctctaccga tgaccatgga gggaaggtcc    2040
atgacaccca ggacttcaag gatgtgctga tgatagagat tgtcaatggg gatttgacct    2100 ggggtttttta acttgtttcg caagtcgtag atgttgacca tgagctcgag gtacatggtc    2160
cattcttttg cttgaagcaa ctgcactaga gttagcaagt acacaacaac aatggtcatg    2220
tcaggtactg tcggcataaa gggacaaaca ggtaaaagtg agatgtaaga gtgaaaaatt    2280
cccgggtcga cgagctcact agtcggcggc cgctctagag gatccaagct tacgtacgcg    2340
tgcatgcgac gtcatagctc ttctatagtg tcacctaaat tcaattcact ggccgtcgtt    2400
ttacaacgtc gtgactggga aaaccctggc gttacccaac ttaatcgcct tgcagcacat    2460
ccccctttcg ccagctggcg taatagcgaa gaggcccgca ccgatcgccc ttcccaacag    2520
ttgcgcagcc tgaatggcga atgg                                           2544
```

<210> SEQ ID NO 2
<211> LENGTH: 318
<212> TYPE: PRT
<213> ORGANISM: Fusarium

<400> SEQUENCE: 2

```
Met Arg Leu Ser Thr Ile Leu Thr Gly Ala Ala Leu Phe Ser Ser
 1               5                  10                  15

Gln Ala Leu Asn Ile Leu Leu Asn Asn Asp Asp Gly Phe Gly Ser Ala
            20                  25                  30

Asn Leu Arg Glu Met Tyr Arg Leu Phe Lys Glu Lys Gly His Asn Val
        35                  40                  45

Trp Leu Val Ala Pro Ala Thr Lys Gln Ser Gly Lys Gly Gly Thr Ser
    50                  55                  60

Asp Phe Thr Thr Glu Gly Asn Leu Thr Gly Pro Ser Gln Tyr Asp Leu
65                  70                  75                  80

Ile Pro Lys Gly Ala Pro Ser Val Gly Ser Asp Pro Lys Asp Ser Gln
                85                  90                  95

Ile Trp Tyr Tyr Asn Gly Thr Pro Ala Ala Cys Thr Phe Val Ala Leu
            100                 105                 110

Asp Tyr Val Leu Pro Arg Tyr Ala Asn Phe Ser Val Pro Asp Leu Val
        115                 120                 125

Val Thr Gly Pro Asn Tyr Gly Thr Asn Leu Gly Gly Phe Val Trp Thr
    130                 135                 140
```

-continued

Leu Ser Gly Thr Ala Gly Ala Ala Tyr Ala Ala Thr Asn Arg Gly Ile
145                 150                 155                 160

Pro Ala Ile Ala Ile Ser Ala Ser Asn Gln Glu Val Pro Tyr Phe Glu
                165                 170                 175

Leu Thr Asn Arg Thr Asn Pro Ala Thr Trp Ala Ala Gln Ala Ser Val
            180                 185                 190

Lys Phe Val Glu Asn Phe Ile Ser Thr Ala Gly Lys Asn Gly Pro Leu
        195                 200                 205

Leu Pro Ile Gly Tyr Gly Val Asn Val Asn Leu Pro Val Leu Thr Lys
    210                 215                 220

Lys Asp His Asp Pro Glu Phe Val Gln Thr Arg Phe Thr Gly Asn Ala
225                 230                 235                 240

His Val Asn Glu Ala Val Leu Asp Pro Lys Lys Gly Thr Phe Thr Trp
                245                 250                 255

Ala Asn Ile Lys Pro Tyr Ala Ala Gly Val Asn Ala Cys Ile Asn Gly
            260                 265                 270

Asn Cys Ser Leu Pro Gly Glu Thr Tyr Val Val Glu Asn Gly Lys Ala
        275                 280                 285

Ser Val Ser Phe Tyr Thr Val Asp Tyr Ser Ala Pro Glu Thr Glu Tyr
    290                 295                 300

Thr Glu Ser Leu Ile Asp Arg Val Ala Ser Phe Ile Gly Lys
305                 310                 315

<210> SEQ ID NO 3
<211> LENGTH: 21
<212> TYPE: DNA
<213> ORGANISM: Fusarium

<400> SEQUENCE: 3
ccatacgaaa ccgcccaagt t                                            21

<210> SEQ ID NO 4
<211> LENGTH: 21
<212> TYPE: DNA
<213> ORGANISM: Fusarium

<400> SEQUENCE: 4
cccatcggtt acggcgtcaa t                                            21

<210> SEQ ID NO 5
<211> LENGTH: 42
<212> TYPE: DNA
<213> ORGANISM: Fusarium

<400> SEQUENCE: 5
gcggatttaa atgatgcgtc tgtcaactat cctcactgga gc                     42

<210> SEQ ID NO 6
<211> LENGTH: 39
<212> TYPE: DNA
<213> ORGANISM: Fusarium

<400> SEQUENCE: 6
gcggttaatt aattatttcc caatgaacga cgccactcg                         39

<210> SEQ ID NO 7
<211> LENGTH: 35
<212> TYPE: DNA
<213> ORGANISM: Fusarium

<400> SEQUENCE: 7
cagtgaattg gcctcgatgg ccgcggccgc gaatt        35

<210> SEQ ID NO 8
<211> LENGTH: 35
<212> TYPE: DNA
<213> ORGANISM: Fusarium

<400> SEQUENCE: 8
aattcgcggc cgcggccatc gaggccaatt cactg        35

<210> SEQ ID NO 9
<211> LENGTH: 34
<212> TYPE: DNA
<213> ORGANISM: Fusarium

<400> SEQUENCE: 9
cacgaaggaa agacgatggc tttcacggtg tctg         34

<210> SEQ ID NO 10
<211> LENGTH: 34
<212> TYPE: DNA
<213> ORGANISM: Fusarium

<400> SEQUENCE: 10
cagacaccgt gaaagccatc gtctttcctt cgtg         34

<210> SEQ ID NO 11
<211> LENGTH: 46
<212> TYPE: DNA
<213> ORGANISM: Fusarium

<400> SEQUENCE: 11
ctatctcttc accatggtac cttaattaaa taccttgttg gaagcg    46

<210> SEQ ID NO 12
<211> LENGTH: 46
<212> TYPE: DNA
<213> ORGANISM: Fusarium

<400> SEQUENCE: 12
cgcttccaac aaggtattta attaaggtac catggtgaag agatag    46

<210> SEQ ID NO 13
<211> LENGTH: 39
<212> TYPE: DNA
<213> ORGANISM: Fusarium

<400> SEQUENCE: 13
gcggttaatt aattatttcc caatgaacga cgccactcg    39

<210> SEQ ID NO 14
<211> LENGTH: 35
<212> TYPE: DNA
<213> ORGANISM: Fusarium

<400> SEQUENCE: 14
gcgggcatgc gtctgtcaac tatcctcact ggagc        35